(12) United States Patent
Chen et al.

(10) Patent No.: US 11,998,564 B2
(45) Date of Patent: Jun. 4, 2024

(54) STABLE CARDIOPLEGIC SOLUTION FOR CARDIAC SURGERY

(71) Applicant: National Taiwan University, Taipei (TW)

(72) Inventors: Yih-Sharng Chen, Taipei (TW); Li-Jiuan Shen, Taipei (TW); Mei-Hsin Lin, Taipei (TW); Heng-Wen Chou, Taipei (TW)

(73) Assignee: National Taiwan University, Taipei (TW)

( * ) Notice: Subject to any disclaimer, the term of this patent is extended or adjusted under 35 U.S.C. 154(b) by 201 days.

(21) Appl. No.: 17/413,567

(22) PCT Filed: Dec. 14, 2018

(86) PCT No.: PCT/US2018/065581
§ 371 (c)(1),
(2) Date: Jun. 13, 2021

(87) PCT Pub. No.: WO2020/122928
PCT Pub. Date: Jun. 18, 2020

(65) Prior Publication Data
US 2022/0088066 A1 Mar. 24, 2022

(51) Int. Cl.
| | | |
|---|---|---|
| *A61K 33/06* | (2006.01) | |
| *A61K 9/08* | (2006.01) | |
| *A61K 31/047* | (2006.01) | |
| *A61K 31/133* | (2006.01) | |
| *A61K 33/04* | (2006.01) | |
| *A61K 33/14* | (2006.01) | |

(52) U.S. Cl.
CPC ........... *A61K 33/06* (2013.01); *A61K 9/08* (2013.01); *A61K 31/047* (2013.01); *A61K 31/133* (2013.01); *A61K 33/04* (2013.01); *A61K 33/14* (2013.01)

(58) Field of Classification Search
CPC ...... A61K 33/06; A61K 33/14; A61K 31/191; A61K 9/08; A61K 33/00
See application file for complete search history.

(56) References Cited

U.S. PATENT DOCUMENTS

| | | | |
|---|---|---|---|
| 4,988,515 A | * | 1/1991 | Buckberg .............. A61K 47/06 514/23 |
| 5,130,230 A | | 7/1992 | Segall |
| 5,256,660 A | | 10/1993 | Swan |
| 5,407,793 A | | 4/1995 | Del Nido |
| 5,462,524 A | | 10/1995 | Powell |
| 5,466,216 A | | 11/1995 | Brown |
| 5,574,019 A | | 11/1996 | Segall |
| 5,747,071 A | | 5/1998 | Segall |
| 6,054,427 A | | 4/2000 | Winslow |
| 6,495,532 B1 | | 12/2002 | Bathurst |
| 9,060,507 B2 | | 6/2015 | Alford |
| 2005/0215937 A1 | | 9/2005 | Spinale |
| 2006/0154357 A1 | | 7/2006 | Hassanein |
| 2007/0243518 A1 | | 10/2007 | Serna |
| 2011/0059177 A1 | | 3/2011 | Thatte |
| 2013/0203041 A1 | | 8/2013 | Franklin |
| 2016/0361337 A1 | | 12/2016 | Antochshuk et al. |
| 2017/0049811 A1 | | 2/2017 | Berry |
| 2017/0143760 A1 | | 5/2017 | Volgushev |

FOREIGN PATENT DOCUMENTS

| | | | |
|---|---|---|---|
| CN | 103893205 A | 7/2014 | |
| JP | 2011512351 A | 4/2011 | |
| RU | 2145843 C1 | 2/2000 | |
| WO | WO1995034301 A1 | 12/1995 | |
| WO | WO2008112323 A1 | 9/2008 | |
| WO | WO 2016/201126 A1 | 12/2016 | |
| WO | WO-2016201126 A1 * | 12/2016 | ........... A01N 1/0226 |
| WO | WO 2017188852 | 11/2017 | |

OTHER PUBLICATIONS

Sanetra (Kardiochir Torakochirurgia Pol, Jun. 25, 2018, vol. 15, pp. 114-118) (Year: 2018).*
Baraka et al. "Lidocaine cardioplegia for prevention of reperfusion ventricular fibrillation." The Annals of thoracic surgery 55.6 (Jun. 1, 1993): 1529-1533.
Matte et al. "History and use of del Nido cardioplegia solution at Boston Children's Hospital." The Journal of extra-corporeal technology 44.3 (Sep. 2012).
Nahas et al. "Guidelines for the treatment of acidaemia with THAM." Drugs 55.2 (Feb. 1, 1998): 191-224.
Chua et al. "Plasma-Lyte 148 vs 0.9% saline for fluid resuscitation in diabetic ketoacidosis." Journal of critical care 27.2 (Apr. 1, 2012): 138-145.

* cited by examiner

*Primary Examiner* — Mark V Stevens
(74) *Attorney, Agent, or Firm* — Rei-Cheng Jason Hsu

(57) ABSTRACT

The present invention is a cardioplegic solution that demonstrates better stability in pH, particulate matter formation and osmolality but at the same time demonstrates superior ability to preserve heart functions than currently available cardioplegic solutions. The cardioplegic solution comprises potassium ($K^+$), magnesium ($Mg^{2+}$), sodium ($Na^+$), chloride ($Cl^-$), gluconate, acetate, sulfate ($SO_4^{2-}$), THAM and mannitol dissolved in water.

22 Claims, 22 Drawing Sheets

*P<0.05 vs. Saline group at the same time point.
P<0.05 vs. KH group at the same time point.
&P<0.05 vs. WAW group at the same time point.

P<0.05 vs. Saline group at the same time point.
†P<0.05 vs. KH group at the same time point.
&P<0.05 vs. WAW group at the same time point.

*P<0.05 vs. Saline group at the same time point.
P<0.05 vs. KH group at the same time point.
&P<0.05 vs. WAW group at the same time point.

*p<0.05 vs. Saline group at the same time point.
p<0.05 vs. KH group at the same time point.
&p<0.05 vs. WAW group at the same time point.

| Ion conc. | mEq/L | del Nido soln.* | WAW sion |
|---|---|---|---|
| Potassium (K⁺) | (mEq/L) | 29.63 | 29.63 |
| Calcium (Ca²⁺) | (mEq/L) | 0.00 | 0.00 |
| Magnesium (Mg²⁺) | (mEq/L) | 18.39 | 18.39 |
| Sodium (Na⁺) | (mEq/L) | 133.80 | 133.80 |
| Chloride (Cl⁻) | (mEq/L) | 118.51 | 118.51 |
| Gluconate | (mmol/L) | 21.98 | 21.98 |
| acetate | (mmol/L) | 25.81 | 25.81 |
| Sulfate (SO₄²⁻) | (mmol/L) | 7.76 | 7.76 |
| Sodium bicarbonate (NaHCO₃) | (mmol/L) | 12.42 | 0.00 |
| THAM | (mmol/L) | 0.00 | 20 or 10 |
| mannitol | | 3115.7 mg | 3115.7 mg |

FIG. 15

| Groups | Plegisol | HTK | DMD | WAW | RH | Saline |
|---|---|---|---|---|---|---|
| ECG (mV) | | | | | | |
| Number/Time points | 0 min | 0 min | 0 min | 0 min | 0 min | 0 min |
| No. 1 | 2.8103 | 4.0993 | 2.2692 | 5.2446 | 5.3997 | 1.21 |
| No. 2 | 3.9854 | 2.3 | 3.5832 | 3.9216 | 4.0736 | 0.21 |
| No. 3 | 1.5964 | 1.497 | 2.3 | 4.63 | 3.4099 | 2.634 |
| No. 4 | 2.001 | 3.2 | 3.2 | 3.4 | 3.9779 | 1.231 |
| No. 5 | 3.21 | 3.4697 | 3.094 | 5.117 | 4.697 | 0.8541 |
| No. 6 | 2.945 | 2.678 | 2.937 | 4.9982 | 5.634 | 0.2674 |
| AVE | 2.76 | 2.94 | 3.00 | 4.61 | 4.64 | 1.03 |
| SD | 0.86 | 1.10 | 0.59 | 0.62 | 1.37 | 0.90 |

FIG. 16A

| Groups | Plegisol | HTK | DMD | WAW | RH | Saline |
|---|---|---|---|---|---|---|
| ECG (mV) | | | | | | |
| Number/Time points | 30 min | 30 min | 30 min | 30 min | 30 min | 30 min |
| No. 1 | 2.7099 | 4.4329 | 1.4598 | 3.2438 | 3.4438 | 1.0997 |
| No. 2 | 3.3893 | 2.091 | 3.8638 | 4.6566 | 4.0336 | 0.316 |
| No. 3 | 1.4797 | 1.591 | 2.1104 | 4.4497 | 4.4494 | 1.364 |
| No. 4 | 1.9051 | 3.014 | 2.9987 | 3.6974 | 1.9869 | 0.321 |
| No. 5 | 3.0788 | 2.547 | 3.264 | 4.997 | 4.521 | 0.564 |
| No. 6 | 2.864 | 1.694 | 3.081 | 4.5321 | 5.551 | 0.216 |
| AVE | 2.56 | 2.71 | 2.81 | 4.26 | 3.96 | 0.68 |
| SD | 0.73 | 1.08 | 0.72 | 0.64 | 1.28 | 0.45 |

FIG. 16B

| Groups | Plegisol | HTK | DMD | WAW | RH | Saline |
|---|---|---|---|---|---|---|
| ECG (mV) | | | | | | |
| Number/Time points | 60 min | 60 min | 60 min | 60 min | 60 min | 60 min |
| No. 1 | 2.0574 | 4.292 | 1.4599 | 3.2279 | 4.5296 | 0.5355 |
| No. 2 | 2.3228 | 1.997 | 3.8698 | 3.091 | 3.8856 | 0.5221 |
| No. 3 | 1.8206 | 1.42 | 2.1364 | 4.5 | 4.5464 | 0.674 |
| No. 4 | 1.6002 | 3.999 | 3.1167 | 3.9642 | 2.0771 | 0.465 |
| No. 5 | 2.367 | 2.697 | 3.169 | 4.3674 | 4.412 | 0.964 |
| No. 6 | 1.697 | 2.4697 | 2.8347 | 4.6697 | 5.124 | 0.1674 |
| AVE | 2.01 | 2.58 | 2.80 | 4.00 | 4.09 | 0.56 |
| SD | 0.43 | 0.96 | 0.68 | 0.71 | 1.05 | 0.26 |

FIG. 16C

| Groups | Plegisol | HTK | DMD | WAW | RH | Saline |
|---|---|---|---|---|---|---|
| ECG (mV) | | | | | | |
| Number/Time points | 90 min | 90 min | 90 min | 90 min | 90 min | 90 min |
| No. 1 | 1.8581 | 3.9945 | 1.3434 | 2.9501 | 3.1019 | 0.321 |
| No. 2 | 1.8186 | 2.0333 | 2.6251 | 3.228 | 3.8465 | 0.487 |
| No. 3 | 1.2416 | 1.4331 | 1.8 | 4.5111 | 4.4494 | 0.551 |
| No. 4 | 1.564 | 3.8174 | 2.9987 | 3.5921 | 1.8591 | 0.331 |
| No. 5 | 2.134 | 2.3067 | 2.687 | 4.0169 | 4.216 | 0.331 |
| No. 6 | 2.314 | 2.221 | 2.7985 | 4.223 | 4.974 | 0.1874 |
| AVE | 1.82 | 2.40 | 2.37 | 3.72 | 3.75 | 0.37 |
| SD | 0.39 | 0.86 | 0.65 | 0.62 | 1.12 | 0.13 |

FIG. 16D

| Groups | Plegisol | HTK | DMD | WAW | RH | Saline |
|---|---|---|---|---|---|---|
| ECG (mV) | | | | | | |
| Number/Time points | 120 min | 120 min | 120 min | 120 min | 120 min | 120 min |
| No. 1 | 1.4167 | 4.0195 | 1.6097 | 2.3613 | 3.1101 | 0.215 |
| No. 2 | 2.074 | 1.8 | 1.9877 | 3.0695 | 2.5525 | 0.224 |
| No. 3 | 1.1789 | 1.31 | 1.7944 | 4.4464 | 4.0116 | 0.321 |
| No. 4 | 1.22 | 2.801 | 1.8 | 3.1116 | 2.9275 | 0.229 |
| No. 5 | 1.136 | 1.24 | 1.964 | 3.0124 | 3.497 | 0.224 |
| No. 6 | 1.967 | 3.497 | 2.001 | 4.0912 | 4.6974 | 0.1524 |
| AVE | 2.76 | 2.94 | 3.03 | 4.01 | 4.64 | 1.03 |
| SD | 0.86 | 1.10 | 0.59 | 0.62 | 1.37 | 0.90 |

| Left ventricular systolic pressure (LVSP, mmHg) Number/Time points | Plegisol 0 min | HTK 0 min | DMD 0 min | WAW 0 min | BH 0 min | Saline 0 min |
|---|---|---|---|---|---|---|
| No. 1 | 58.0154 | 23.1497 | 26.8896 | 105.9649 | 100.7956 | 10.111 |
| No. 2 | 20.6741 | 20.115 | 50.7581 | 69.3228 | 52.3254 | 28.312 |
| No. 3 | 16.1226 | 9.4567 | 60.031 | 99.987 | 98.8694 | 6.514 |
| No. 4 | 30.1114 | 30.116 | 59.496 | 82.111 | 119.9988 | 12.634 |
| No. 5 | 38.15 | 38.56 | 69.657 | 90.654 | 105.56 | 36.641 |
| No. 6 | 56.91 | 17.36 | 51.567 | 62.134 | 99.3691 | 15.321 |
| AVE | 36.67 | 23.14 | 53.23 | 85.03 | 96.15 | 18.26 |
| SD | 17.82 | 11.59 | 12.75 | 17.32 | 9.95 | 11.69 |

FIG. 17B

| Left ventricular systolic pressure (LVSP, mmHg) Number/Time points | Plegisol 30 min | HTK 30 min | DMD 30 min | WAW 30 min | BH 30 min | Saline 30 min |
|---|---|---|---|---|---|---|
| No. 1 | 58.9221 | 22.9786 | 20.5816 | 101.1379 | 103.8899 | 9.634 |
| No. 2 | 22.7456 | 24.1897 | 40.6698 | 68.4977 | 67.6761 | 16.521 |
| No. 3 | 10.4285 | 8.654 | 54.211 | 94.15 | 98.291 | 7.145 |
| No. 4 | 27.614 | 24.155 | 55.599 | 79.994 | 101.4626 | 10.697 |
| No. 5 | 36.4289 | 30.964 | 40.31 | 82.641 | 107.011 | 17.31 |
| No. 6 | 34.567 | 10.697 | 26.866 | 60.167 | 95.011 | 9.63 |
| AVE | 31.78 | 20.25 | 39.16 | 81.15 | 100.09 | 11.82 |
| SD | 15.40 | 8.69 | 11.61 | 17.71 | 9.04 | 4.12 |

FIG. 17C

| Left ventricular systolic pressure (LVSP, mmHg) Number/Time points | Plegisol 60 min | HTK 60 min | DMD 60 min | WAW 60 min | BH 60 min | Saline 60 min |
|---|---|---|---|---|---|---|
| No. 1 | 40.7778 | 16.3499 | 11.902 | 67.9444 | 100.651 | 7.2145 |
| No. 2 | 11.2264 | 21.4697 | 34.172 | 68.796 | 93.1266 | 9.654 |
| No. 3 | 12.3362 | 8.124 | 50.094 | 92.354 | 84.4199 | 5.631 |
| No. 4 | 25.5698 | 20.9874 | 22.3 | 78.114 | 99.6634 | 11.974 |
| No. 5 | 22.114 | 19.647 | 46.457 | 80.164 | 100.221 | 6.327 |
| No. 6 | 22.654 | 4.671 | 21.0354 | 59.1297 | 91.334 | 10.367 |
| AVE | 22.18 | 16.02 | 30.97 | 74.31 | 94.90 | 8.53 |
| SD | 10.58 | 6.02 | 15.16 | 10.68 | 6.55 | 2.51 |

FIG. 17D

| Left ventricular systolic pressure (LVSP, mmHg) Number/Time points | Plegisol 90 min | HTK 90 min | DMD 90 min | WAW 90 min | BH 90 min | Saline 90 min |
|---|---|---|---|---|---|---|
| No. 1 | 25.3555 | 8.3424 | 11.5546 | 74.899 | 96.0724 | 6.1254 |
| No. 2 | 11.1913 | 17.564 | 26.0363 | 44.4714 | 82.1615 | 3.664 |
| No. 3 | 13.2745 | 7.984 | 45.1003 | 89.1273 | 92.2695 | 3.337 |
| No. 4 | 24.1587 | 14.974 | 14.978 | 75.102 | 90.8554 | 8.9345 |
| No. 5 | 18.4567 | 16.9457 | 45.126 | 75.124 | 95.511 | 8.64 |
| No. 6 | 21.1179 | 6.6612 | 20.654 | 59.631 | 91.0014 | 12.36 |
| AVE | 18.92 | 12.15 | 26.92 | 69.55 | 90.65 | 7.18 |
| SD | 5.75 | 5.04 | 14.22 | 15.63 | 5.08 | 3.47 |

FIG. 17E

| Left ventricular systolic pressure (LVSP, mmHg) Number/Time points | Plegisol 120 min | HTK 120 min | DMD 120 min | WAW 120 min | BH 120 min | Saline 120 min |
|---|---|---|---|---|---|---|
| No. 1 | 20.5143 | 6.4107 | 11.9884 | 69.9657 | 109.74 | 4.9321 |
| No. 2 | 8.1331 | 13.6974 | 19.3623 | 38.9091 | 92.9196 | 1.234 |
| No. 3 | 9.9697 | 9.124 | 29.9987 | 89.514 | 85.9771 | 2.111 |
| No. 4 | 22.1114 | 8.8634 | 11.214 | 67.164 | 91.7523 | 3.567 |
| No. 5 | 10.32 | 15.63 | 40.66 | 72.164 | 66.912 | 9.46 |
| No. 6 | 20.361 | 5.6 | 19.631 | 55.631 | 99.321 | 8.31 |
| AVE | 15.23 | 9.89 | 22.05 | 65.53 | 89.33 | 4.94 |
| SD | 6.38 | 3.99 | 11.31 | 17.05 | 6.71 | 3.33 |

STABLE CARDIOPLEGIC SOLUTION FOR CARDIAC SURGERY

CROSS REFERENCE TO RELATED APPLICATIONS

The present invention claims priority to PCT patent application no. PCT/US18/65581 entitled "A STABLE CARDIOPLEGIC SOLUTION FOR CARDIAC SURGERY" filed on Dec. 14, 2018.

FIELD OF THE INVENTION

The present invention relates to the field of cardioplegic solutions. In particular it relates to a cardioplegic solution that demonstrates stability in pH, particulate formation and osmolality while at the same time preserves heart functions.

BACKGROUND OF THE INVENTION

Cardioplegic solutions are used to induce cardioplegia while at the same time preserve a heart's viability for purposes such as cardiac surgery. For example, a cardioplegic solution may induce temporary cessation of myocardial activity by way of modified depolarization, reduce energy consumption of the organ, promote anaerobic glycolysis during cardioplegia, block the detrimental accumulation of calcium ions in myocardial cells, scavenge hydrogen ions and preserve high-energy phosphates. As a crucial component of cardiac surgery, a cardioplegic solution should be stable in storage and clinical use, simple to prepare and use, quick to induce cardioplegia that lasts for the duration of the cardiac surgery as required, preserves crucial heart functions and bears reasonable costs.

Some commonly used cardioplegic solutions are Custodiol® HTK, Plegisol®, and the del Nido solution. Custodiol® HTK is characterized by its low sodium and calcium ion concentrations of 15 mEq/L and 0.015 mEq/L, respectively, thus achieving cardioplegia by way of hyperpolarized arrest. The solution uses histidine as a buffer and comprises tryptophan and ketoglutarate among other components. Though it has a long working duration of up to 4 hours, and a shelf life of up to a year at 2 to 8 degrees centigrade, clinical use of Custodiol® HTK is limited by its relatively expensive price estimated to be over USD$1000 per 1,000 mL in the US which is more than four times the price of Plegisol® discussed next.

A more affordable option is Plegisol®, a cardioplegic solution that achieves depolarized arrest with a relatively high potassium ion concentration of 16 mEq/L. Though this solution may be stored at room temperature for up to 2 years, it is limited by a short working duration of 20 to 30 minutes as compared to up to two hours duration sometimes required by open heart surgery. Plegisol is also limited by shortages in the market caused by manufacturing delay.[1,2]

[1] https://www.beaumont.org/treatments/heart-surgery-frequently-asked-questions
[2] https://www.ashp.org/drug-shortages/current-shortages/Drug-Shortage-Detail.aspx?id=121

A third option is del Nido cardioplegic solution. The del Nido solution comprises 16.3 mL of 20% mannitol, 4 mL of 50% magnesium sulfate, 13 mL of 8.4% sodium bicarbonate and 3 mL of 2 mEq/mL potassium chloride mixed with per liter of Plasma-Lyte A solution. The Plasma-Lyte A solution contains per liter 140 mEq/L sodium $Na^+$, 5 mEq/L potassium $K^+$, 3 mEq/L magnesium $Mg^{2+}$, 98 mEq/L chloride $Cl^-$, 27 mEq/L acetate, and 23 mEq/L gluconate. In addition, 13 mL of 1% lidocaine and 20% fully oxygenated blood from the patient may optionally be added to the solution. Composition of the crystalloid component of the del Nido solution is shown in FIG 15 prior to addition of the optional lidocaine and oxygenated blood from the patient. The del Nido solution has the advantages of hyperkalemia as well as the absence of calcium ions that can enter myocardial cells to the detriment of the patient's health. Additionally, a single dose of the del Nido solution is sufficient to induce cardioplegia, thus minimizing possible heart damage caused by additional administration of cardioplegic solution as well as simplifying the surgical process. The del Nido solution is unpatented, though del Nido does have a U.S. Pat. No. 5,407,793 claiming a different cardioplegic solution that comprises histidine, at least one energy providing material (glucose or fructose), $Na^+$, $K^+$, adenosine, regular insulin, lidocaine and $Ca^{2+}$. Notably, neither the del Nido cardioplegic solution nor the cardioplegic solution of the present invention contain adenosine, histidine nor insulin.

Despite these advantages, the del Nido solution has a short shelf life of 45 days stored at 2 to 8 degrees centigrade. In addition, sterilization by heating results in precipitates or particulate matter as demonstrated in particulate matter example below in connection with FIGS. 4A and 4B below. Since filter sterilization is substantially more expensive than heat sterilization, commercialization of a cardioplegic solution often requires heat sterilization as part of the manufacturing process. However, the formation of particulate matter from heat sterilization renders the del Nido solution unusable. Because of such a short shelf life and formation of particulate matter as result of heat sterilization, there is currently no ready-made off-the-shelf del Nido solution that has been commercialized, and the current practice is to mix the del Nido solution as part of the open heart surgery or order from outsourcing sterile compounding companies. This leads to another disadvantage of the del Nido solution which is that preparation of the solution introduces risk of human error to the surgery. Therefore, there is a need for a cardioplegic solution that works at least as effectively as the del Nido solution in terms of inducing cardiplegia as well as preserving heart functions but without the disadvantages of short shelf life and formation of particulate matter from heat sterilization so that the improved cardioplegic solution is commercializable in ready-made off-the-shelf form so as to substantially minimize requirements for mixing the solution before use.

SUMMARY OF THE INVENTION n/a

15 with 10 mmol/L THAM, cardioplegic solution of the present invention WAW formulation of FIG. 15 with 20 mmol/L THAM as well as the del Nido solution treated with heat sterilization process and the del Nido solution treated with filter sterilization process, respectively, stored at 16° C.

Figure 3:
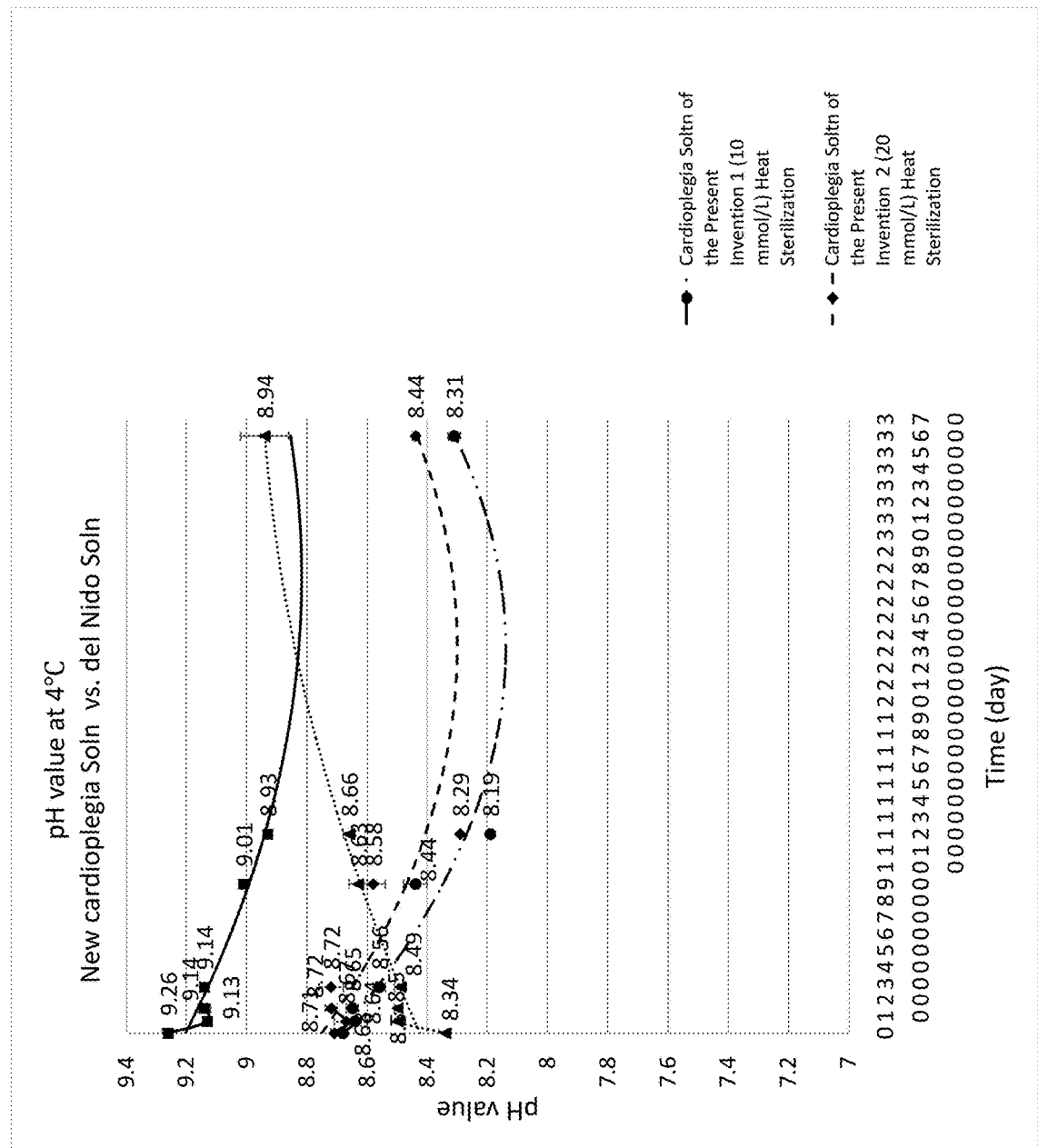

FIG. 3 is a graph with pH value on the Y axis and number of days indicated on the X axis comparing pH value of the cardioplegic solution under study including the cardioplegic solution of the present invention WAW formulation of FIG. 15 with 10 mmol/L THAM, cardioplegic solution of the present invention WAW formulation of FIG. 15 with 20 mmol/L THAM as well as the del Nido solution treated with heat sterilization process and the del Nido solution treated with filter sterilization process, respectively, stored at 4° C.

Figures 4A, 4B:
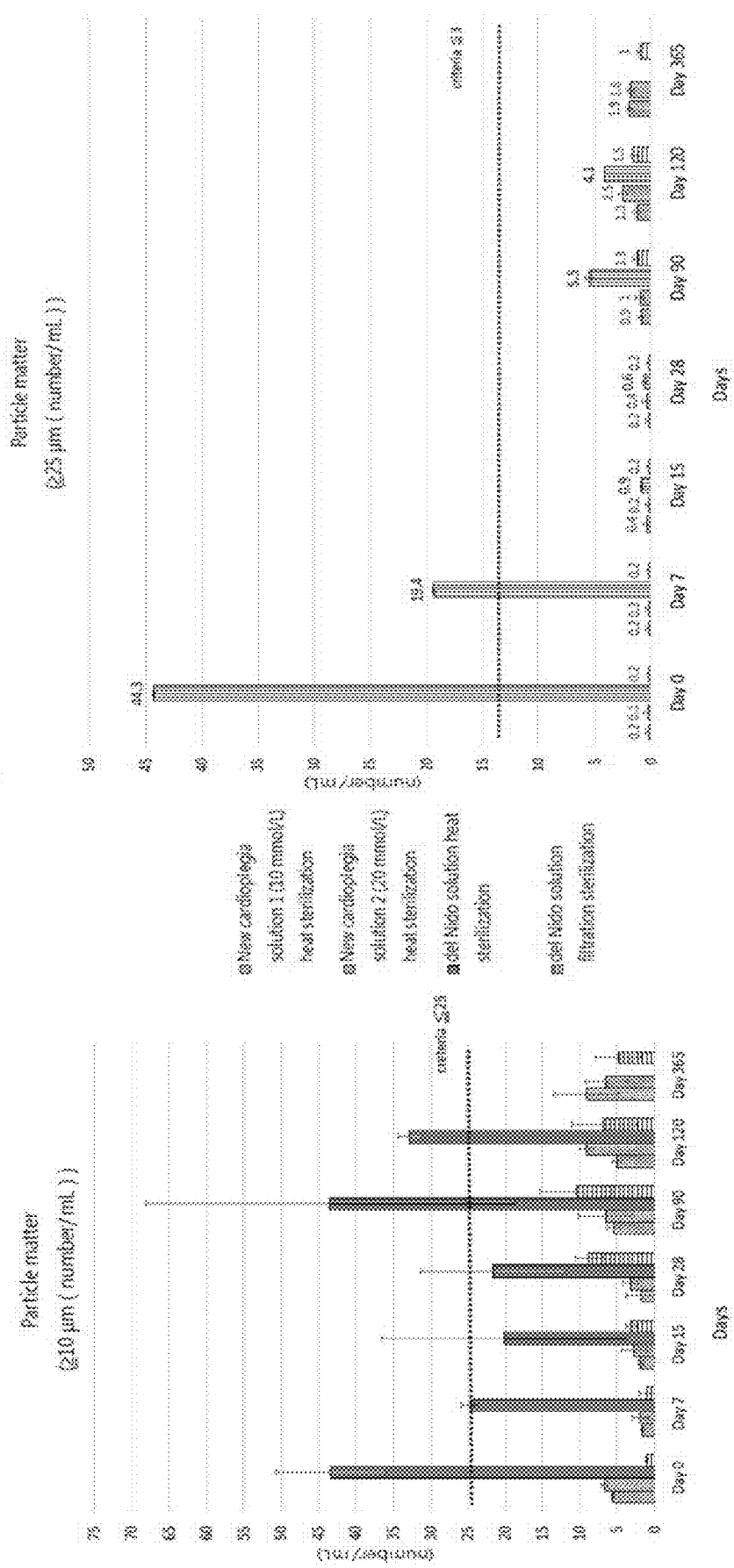

FIGS. 4A and 4B are graphs with number of particles/mL on the Y axis and number of days on the X axis comparing particulate matter concentration of particulate matter size>=10 µm and of particular matter size>=25 µm, respectively, for the four cardioplegic solutions under study including the cardioplegic solution of the present invention WAW formulation of FIG. 15 with 10 mmol/L THAM, cardioplegic solution of the present invention WAW formulation of FIG. 15 with 20 mmol/L THAM as well as the del Nido solution treated with heat sterilization process and the del Nido solution treated with filter sterilization process, respectively, stored at room temperature.

Figure 5:
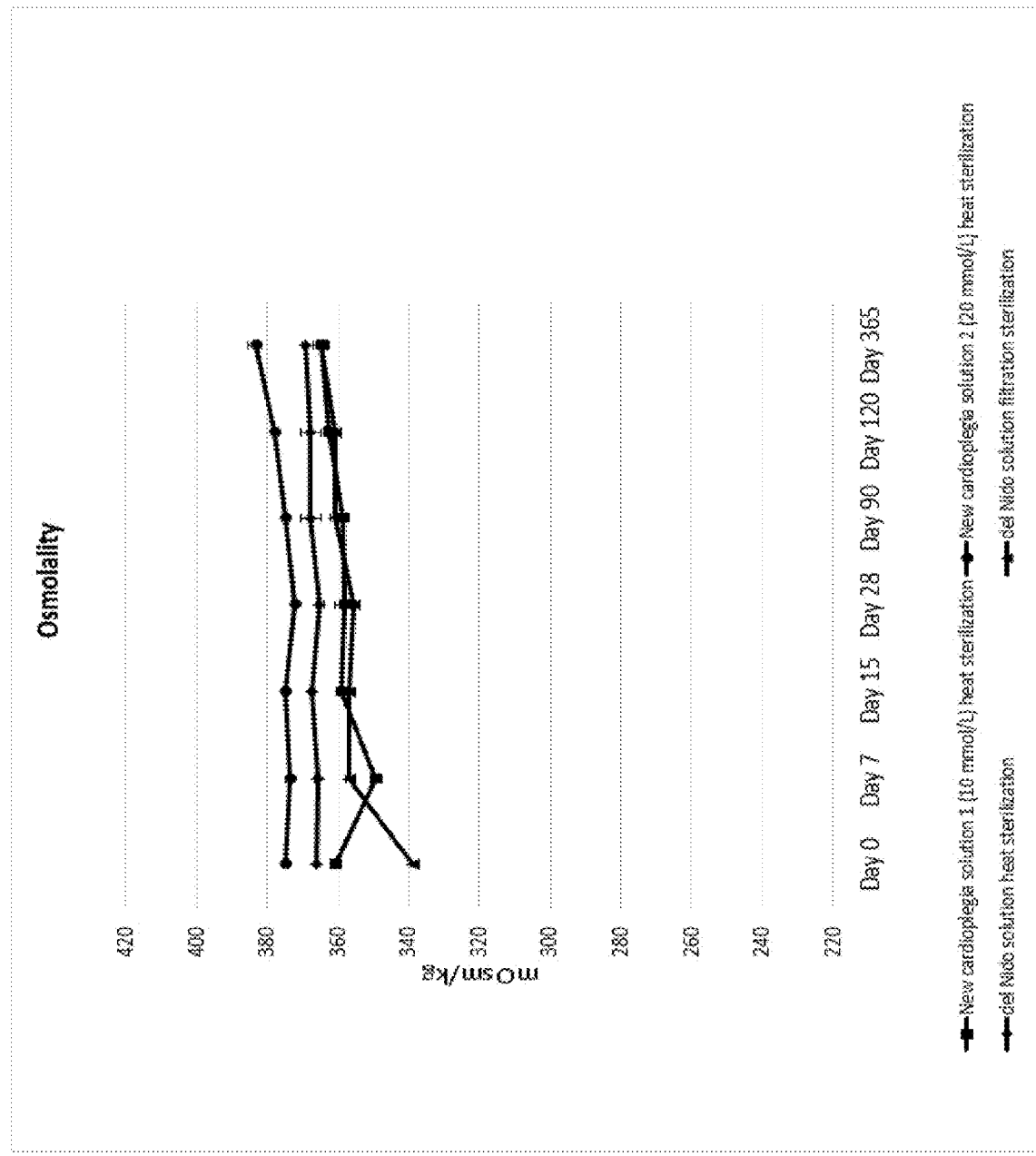

FIG. 5 is a graph with mOsm/kg on the Y axis and number of days on the X axis comparing osmolality of the four cardioplegic solutions under study including the cardioplegic solution of the present invention WAW formulation of FIG. 15 with 10 mmol/L THAM, cardioplegic solution of the present invention WAW formulation of FIG. 15 with 20 mmol/L THAM as well as the del Nido solution treated with heat sterilization process and the del Nido solution treated with filter sterilization process, respectively, stored at room temperature.

Figure 6A:
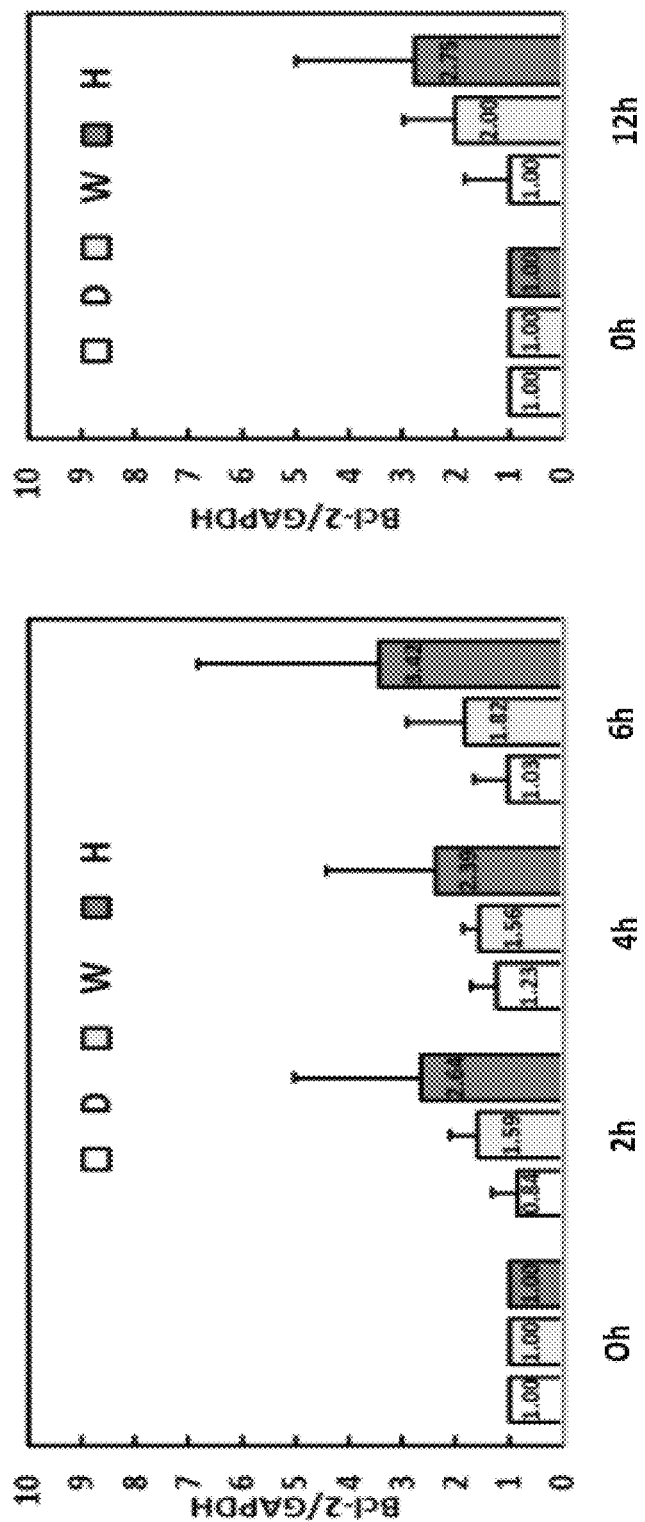
Figure 6B:
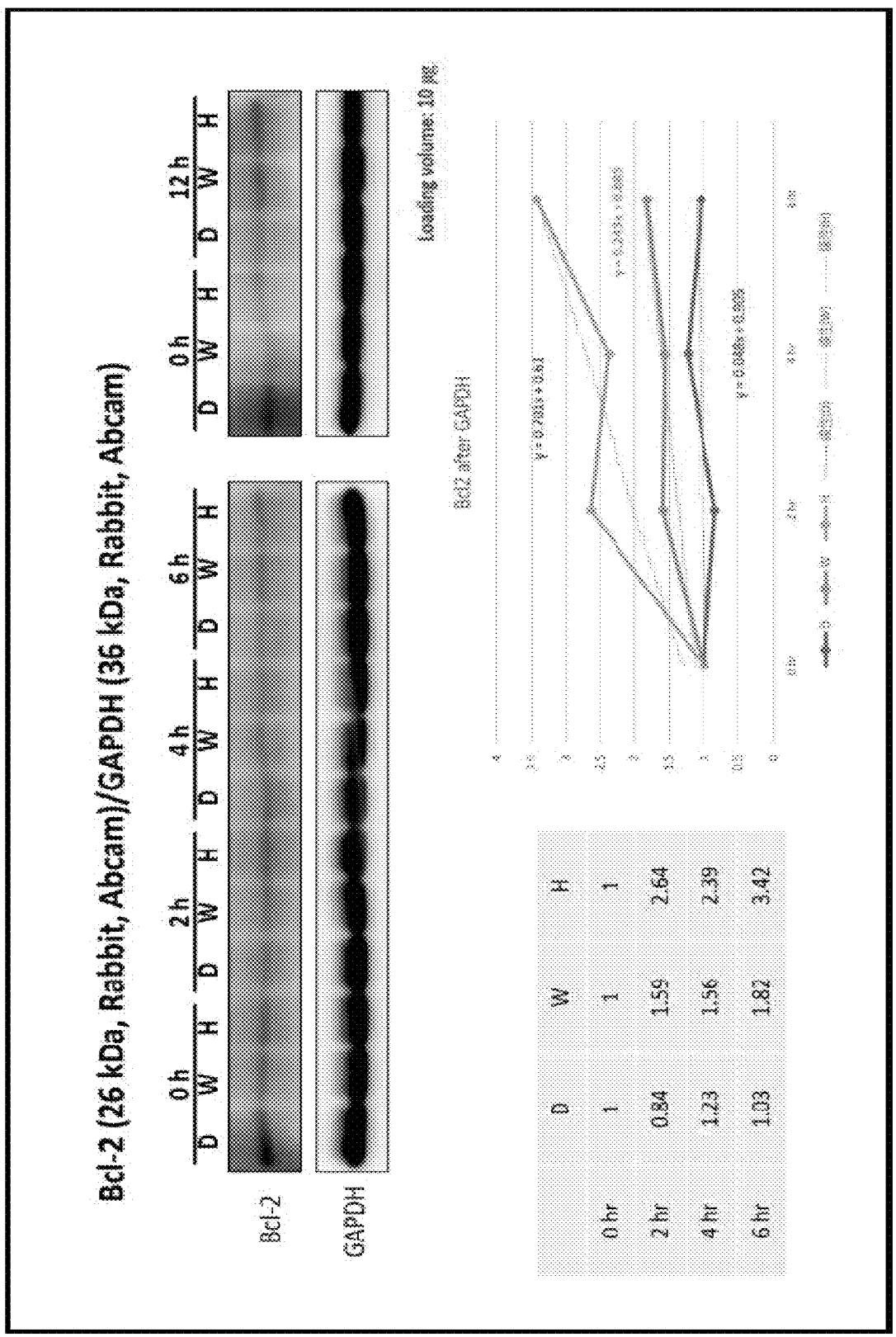

FIGS. 6A and 6B illustrate expression of Bcl-2 in rat heart treated with each of the three cardioplegic solutions under study including the cardioplegic solution of the present invention WAW formulation of FIG. 15 with 20 mmol/L THAM concentration labelled as W, the del Nido cardioplegic solution labelled as D and HTK cardioplegic solution labelled as H.

Figure 7:
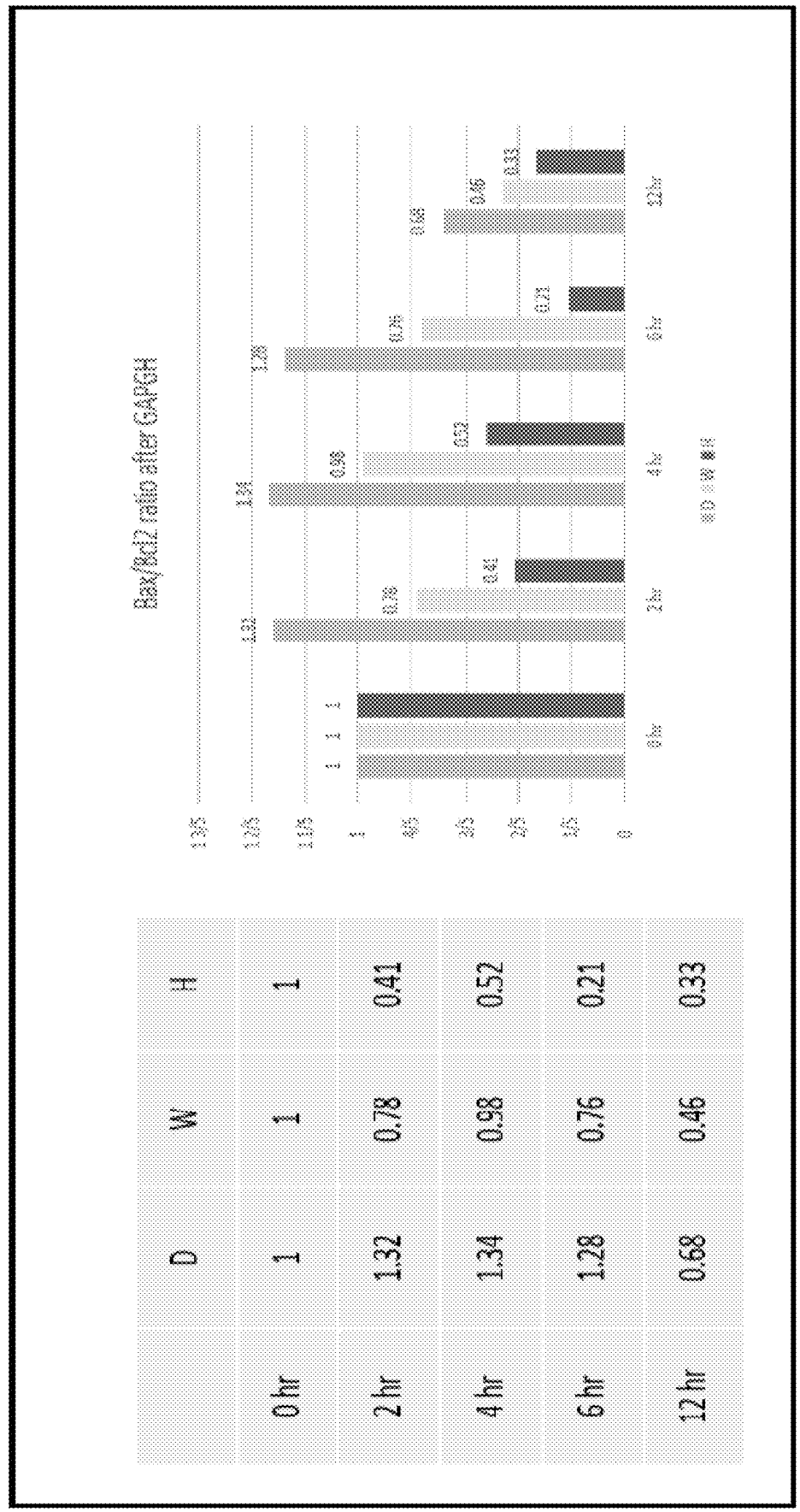

FIG. 7 illustrates Bax/Bcl-2 ratio of rat heart treated with each of the three cardioplegic solutions under study including the cardioplegic solution of the present invention WAW formulation of FIG. 15 with 20 mmol/L THAM concentration labelled as WAW, the del Nido cardioplegic solution labelled as DND and HTK cardioplegic solution labelled as HTK.

Figure 8:
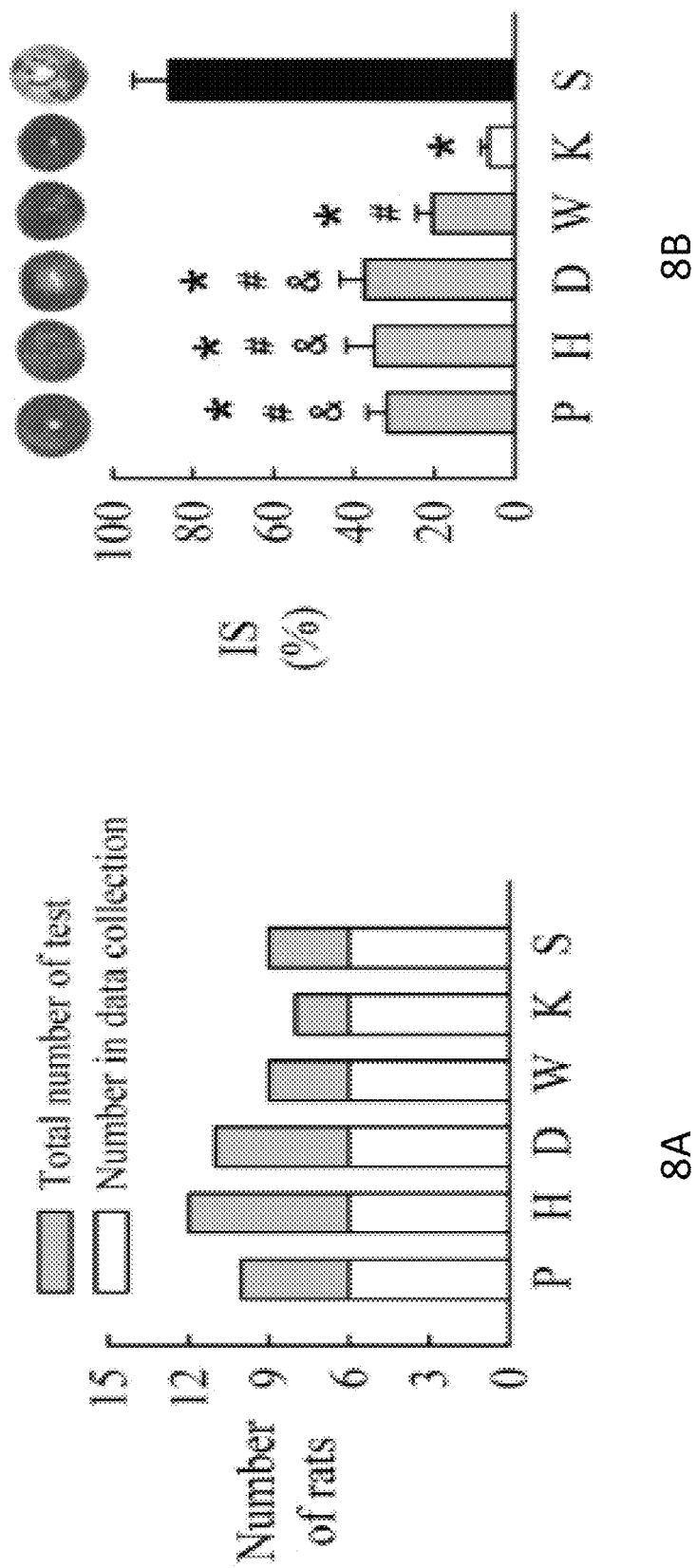

FIGS. 8A and 8B illustrate survival rate of rat heart and heart cells. Specifically FIG. 8A is a graph with number of rats on the Y axis and the cardioplegic solution used on the X axis comparing the number of total rats needed to achieve the required n=6 data points for each of the five solutions under study indicated on the X axis including Plegisol cardioplegic solution labelled P, HTK cardioplegic solution labelled H, the del Nido cardioplegic solution labelled D, the cardioplegic solution of the present invention WAW formulation of FIG. 15 with 20 mmol/L THAM concentration labelled as W, the positive control KH buffer solution labelled K and the negative control saline solution labelled S. FIG. 8B is a graph with ischemic percentage in % on the Y axis and the corresponding cardioplegic solution used on the X axis comparing the percentage of myocardial cells that died from ischemia for rat hearts treated with each of the five solutions under study indicated on the X axis including Plegisol cardioplegic solution labelled P, HTK cardioplegic solution labelled H, the del Nido cardioplegic solution labelled as D, the cardioplegic solution of the present invention WAW formulation of FIG. 15 with 20 mmol/L THAM concentration labelled as W, the positive control KH buffer solution labelled K and the negative control saline solution labelled S.

Figure 9:
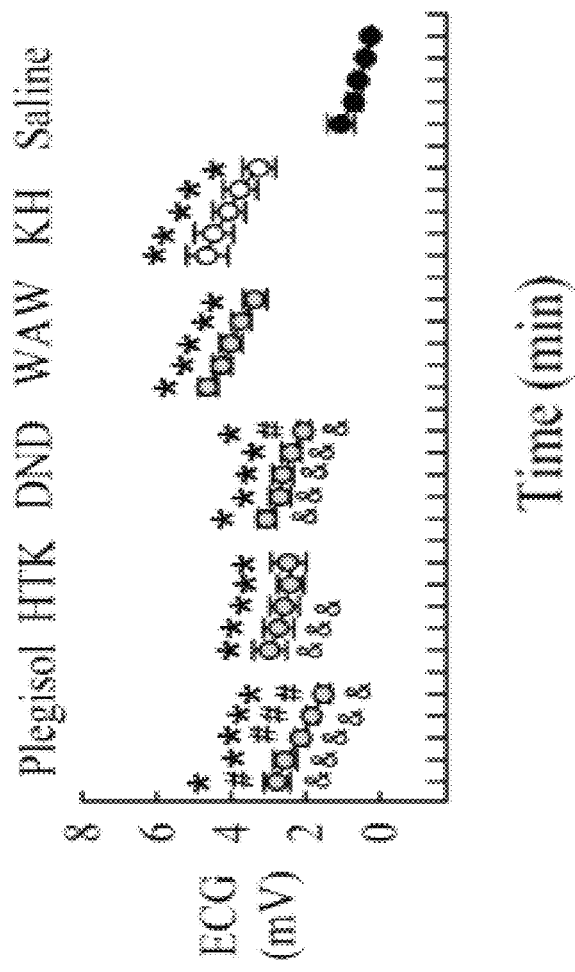

FIG. 9 is a comparison of electrocardiography (ECG) in mV on the Y axis and time on the X axis. The ECG is measured of rat hearts treated with each of the five solutions under study indicated including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figure 10:
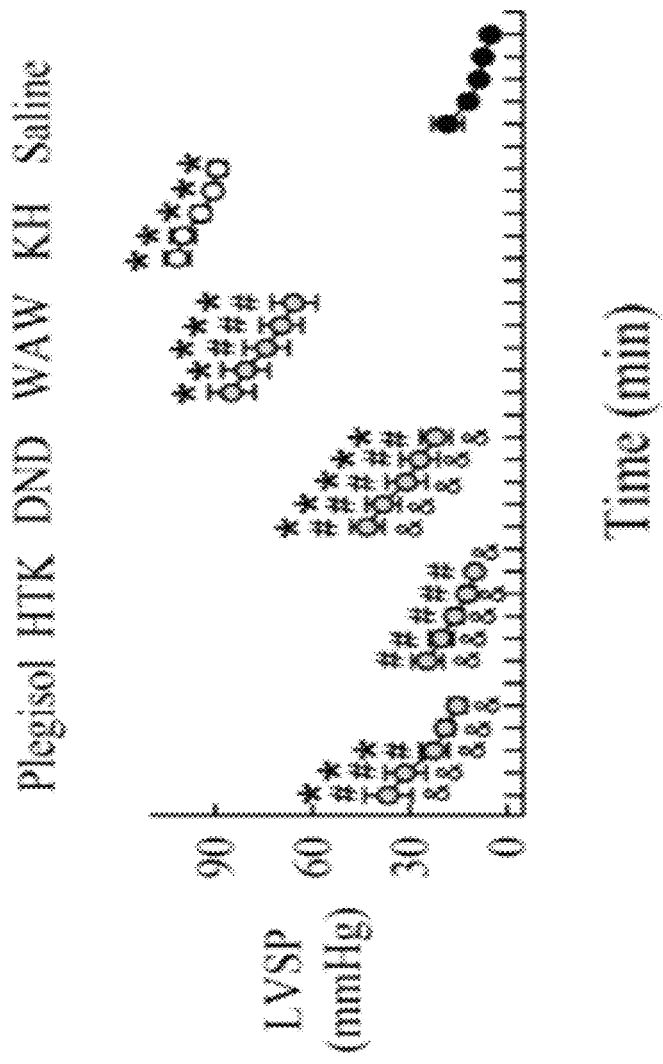

FIG. 10 is a comparison of left ventricle systolic pressure (LVSP) in mmHg on the Y axis and time on the X axis. The LVSP is measured of rat hearts treated with each of the five solutions under study indicated including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figure 11:
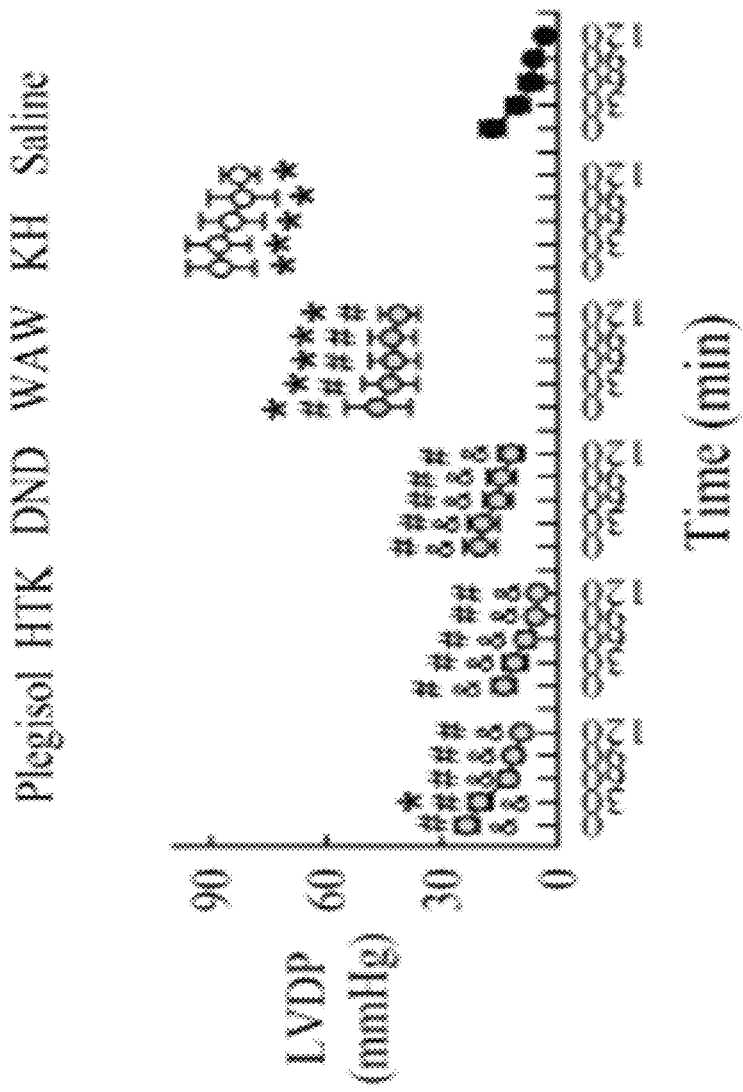

FIG. 11 is a comparison of left ventricle diastolic pressure (LVDP) in mmHg on the Y axis and time on the X axis. The LVDP is measured of rat hearts treated with each of the five solutions under study indicated including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH on the X axis and the negative control saline solution labelled Saline.

Figure 12:
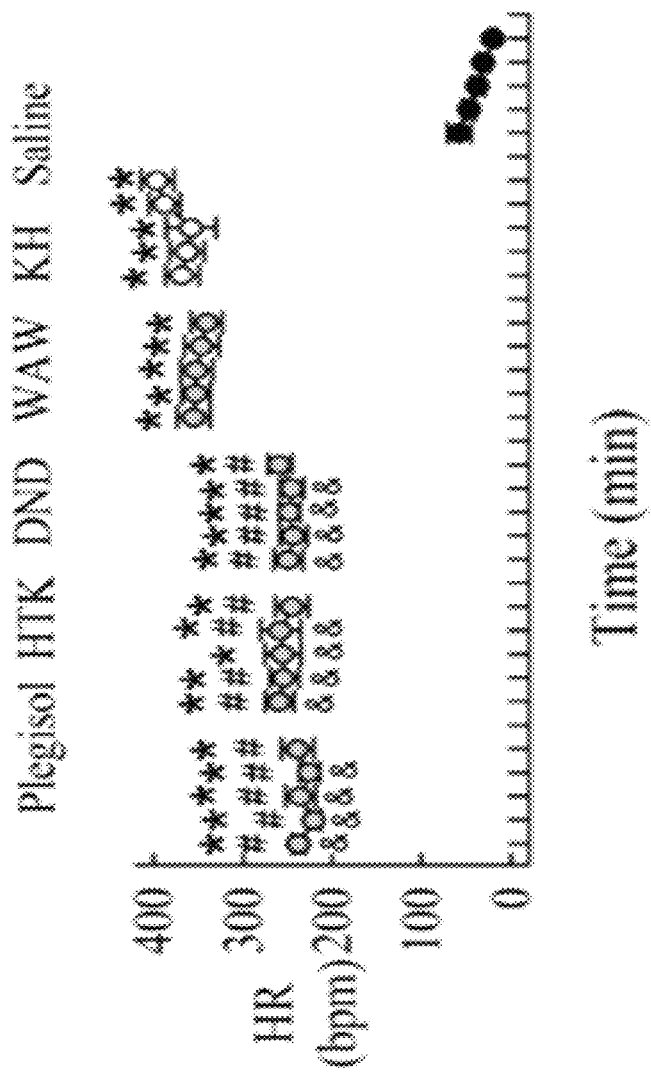

FIG. 12 is a comparison of Heart Rate (HR) in bpm on the Y axis and time on the X axis. The HR is measured of rat hearts treated with each of the five solutions under study indicated including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figure 13:
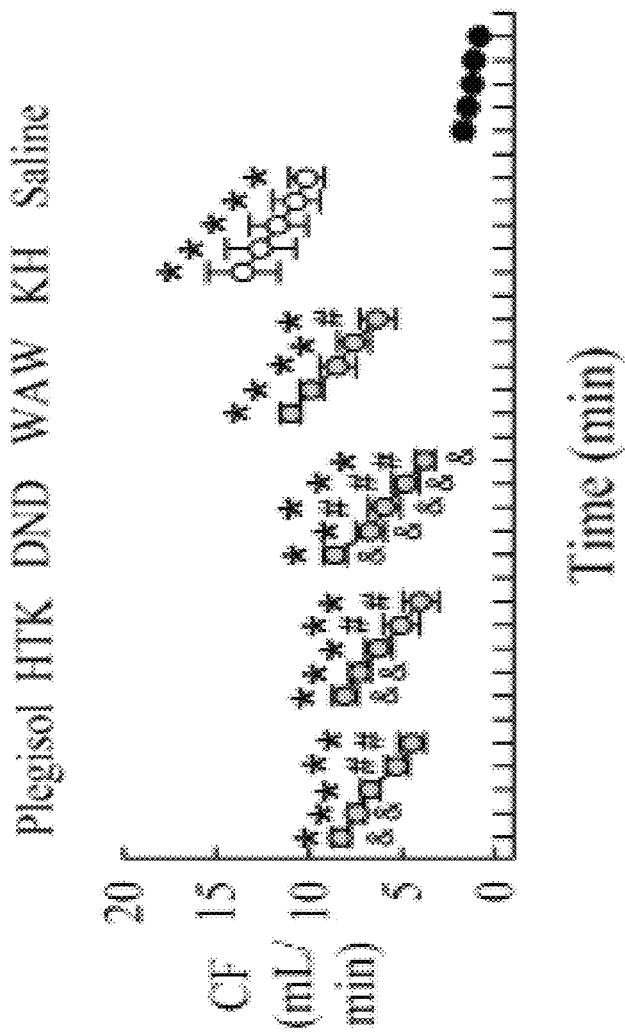

FIG. 13 is a comparison of coronary flow (CF) in mL/min on the Y axis and time on the X axis. The CF is measured of rat hearts treated with each of the five solutions under study indicated including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figure 14:
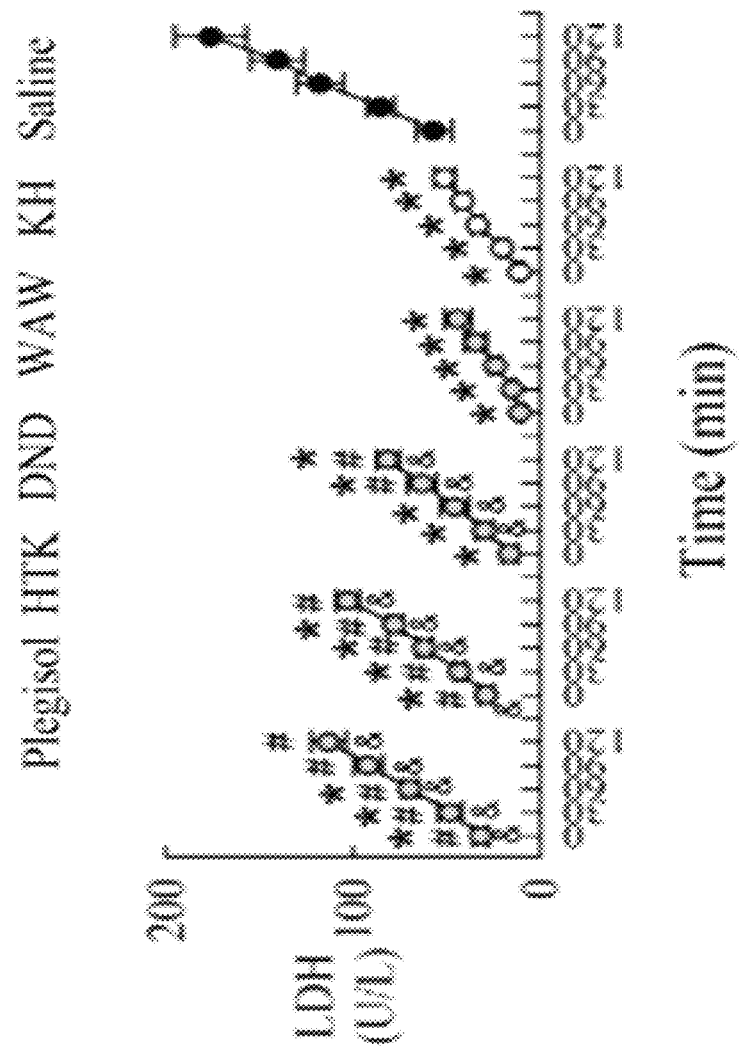

FIG. 14 is a comparison of lactate dehydrogenase (LDH) expression in U/L on the Y axis and time on the X axis. The LDH is measured of rat hearts treated with each of the five solutions under study indicated including Plegisol cardioplegic solution labelled Plegisol, HTK cardioplegic solution labelled HTK, the del Nido cardioplegic solution labelled as DND, the cardioplegic solution WAW formulation of the present invention of FIG. 15 with 20 mmol/L THAM concentration labelled as WAW, the positive control KH buffer solution labelled KH and the negative control saline solution labelled Saline.

FIG. 15 provides ion composition and concentration of the del Nido solution and an embodiment of the cardioplegic solution of the present invention labelled WAW solution dissolved in water.

FIG. 16 shows data underlying FIG. 9 which is a comparison of electrocardiography (ECG) in mV over time of rat hearts treated with each of the five solutions under study including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

FIG. 17 shows data underlying FIG. 10 which is a comparison of left ventricle systolic pressure (LVSP) in mmHg over time of rat hearts treated with each of the five solutions under study including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figures 18A, 18B, 18C, 18D, 18E:
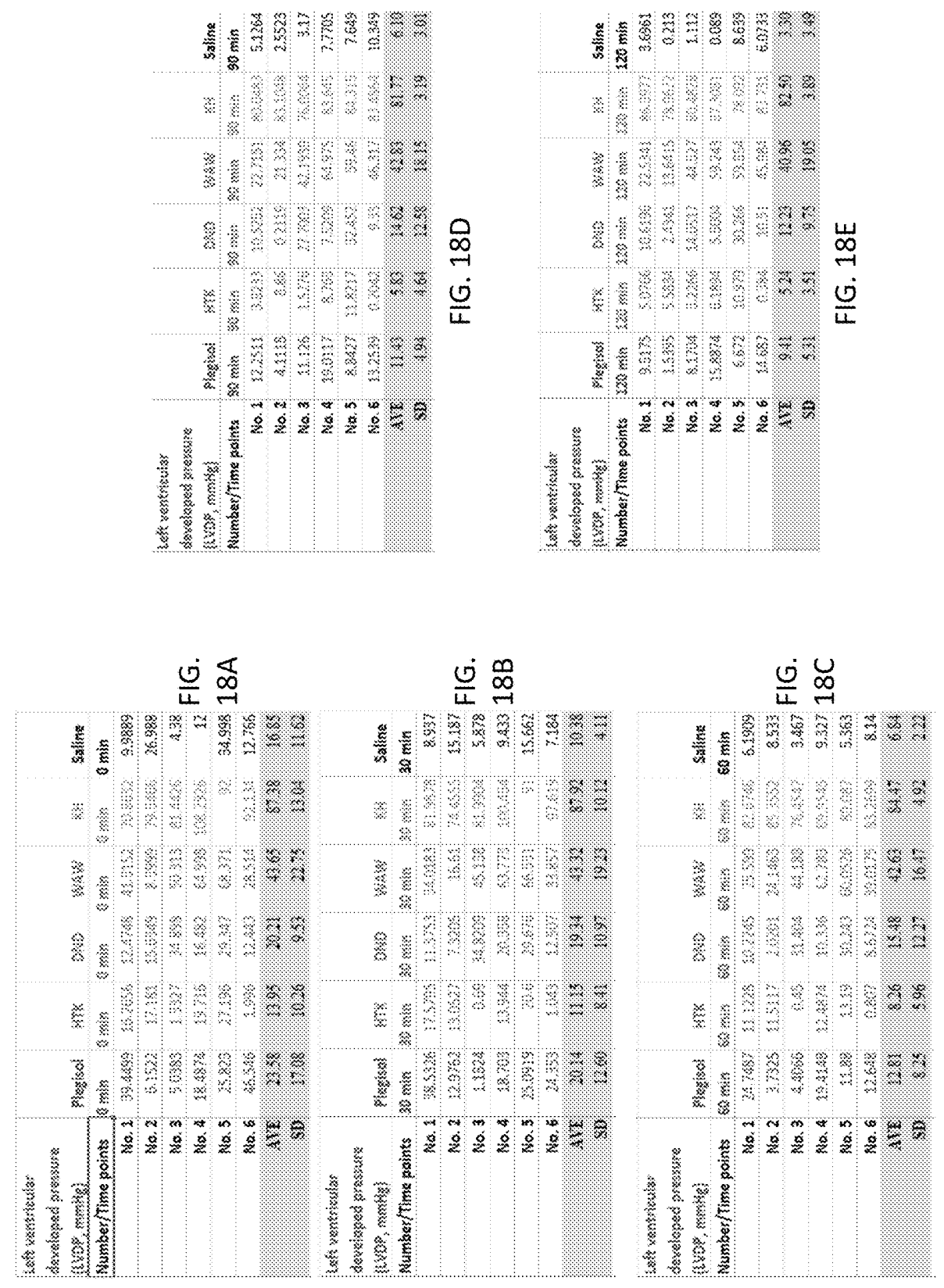

FIG. 18 shows data underlying FIG. 11 which is a comparison of left ventricle diastolic pressure (LVDP) in mmHg over time of rat hearts treated with each of the five solutions under study including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH on the X axis and the negative control saline solution labelled Saline.

Figures 19A, 19B, 19C, 19D, 19E:
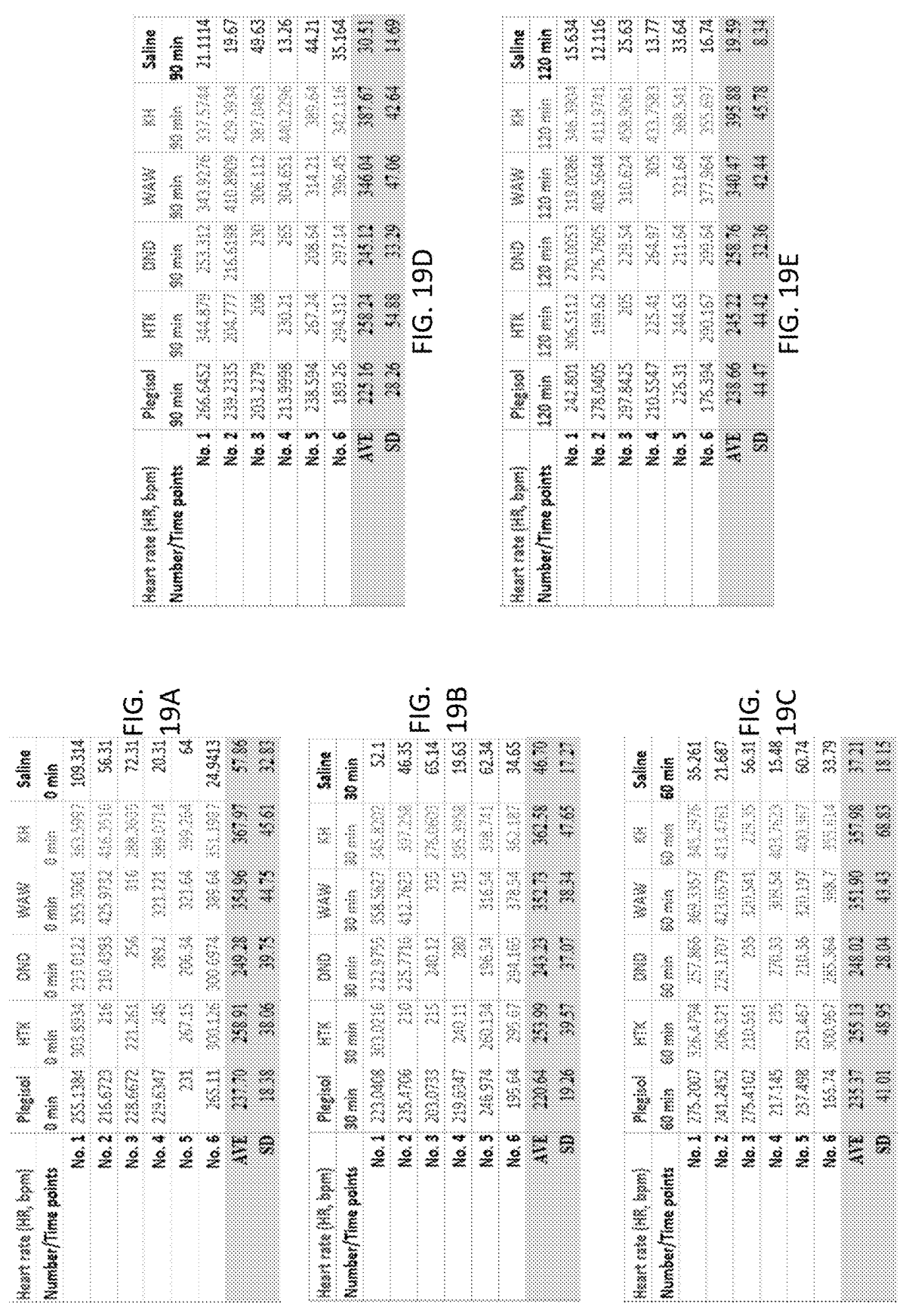

FIG. 19 shows data underlying FIG. 12 which is a comparison of Heart Rate (HR) in bpm over time of rat hearts treated with each of the five solutions under study including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figures 20A, 20B, 20C, 20D, 20E:
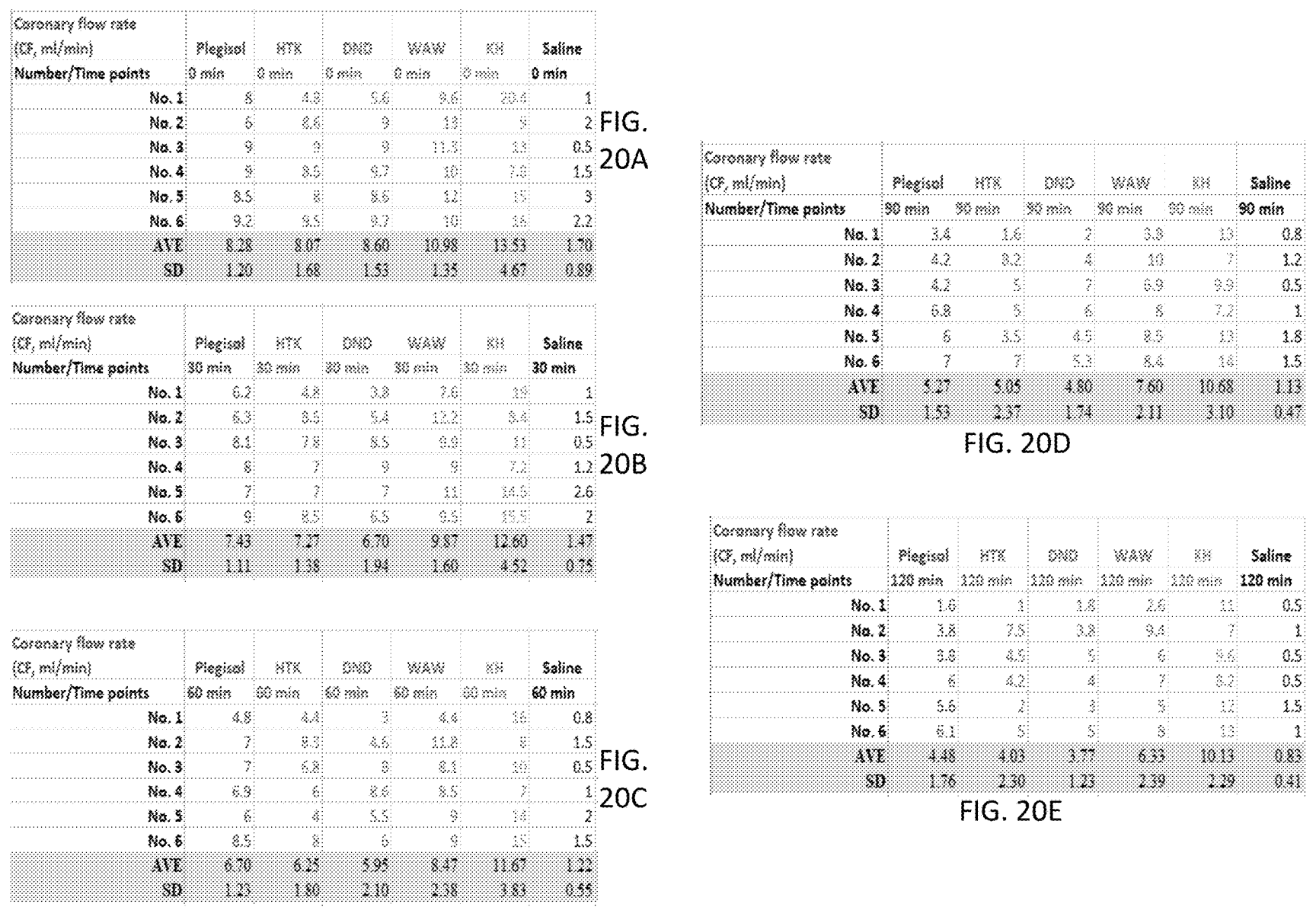

FIG. 20 shows data underlying FIG. 14 which is a comparison of coronary flow (CF) in mL/min over time of rat hearts treated with each of the five solutions under study including Plegisol cardioplegic solution labelled Plegisol, HTK cardioplegic solution labelled HTK, the del Nido cardioplegic solution labelled as DND, the cardioplegic solution of the present invention WAW formulation of FIG. 15 with 20 mmol/L THAM concentration labelled as WAW, the positive control KH buffer solution labelled KH and the negative control saline solution labelled Saline.

Figures 21A, 21B, 21C, 21D, 21E:
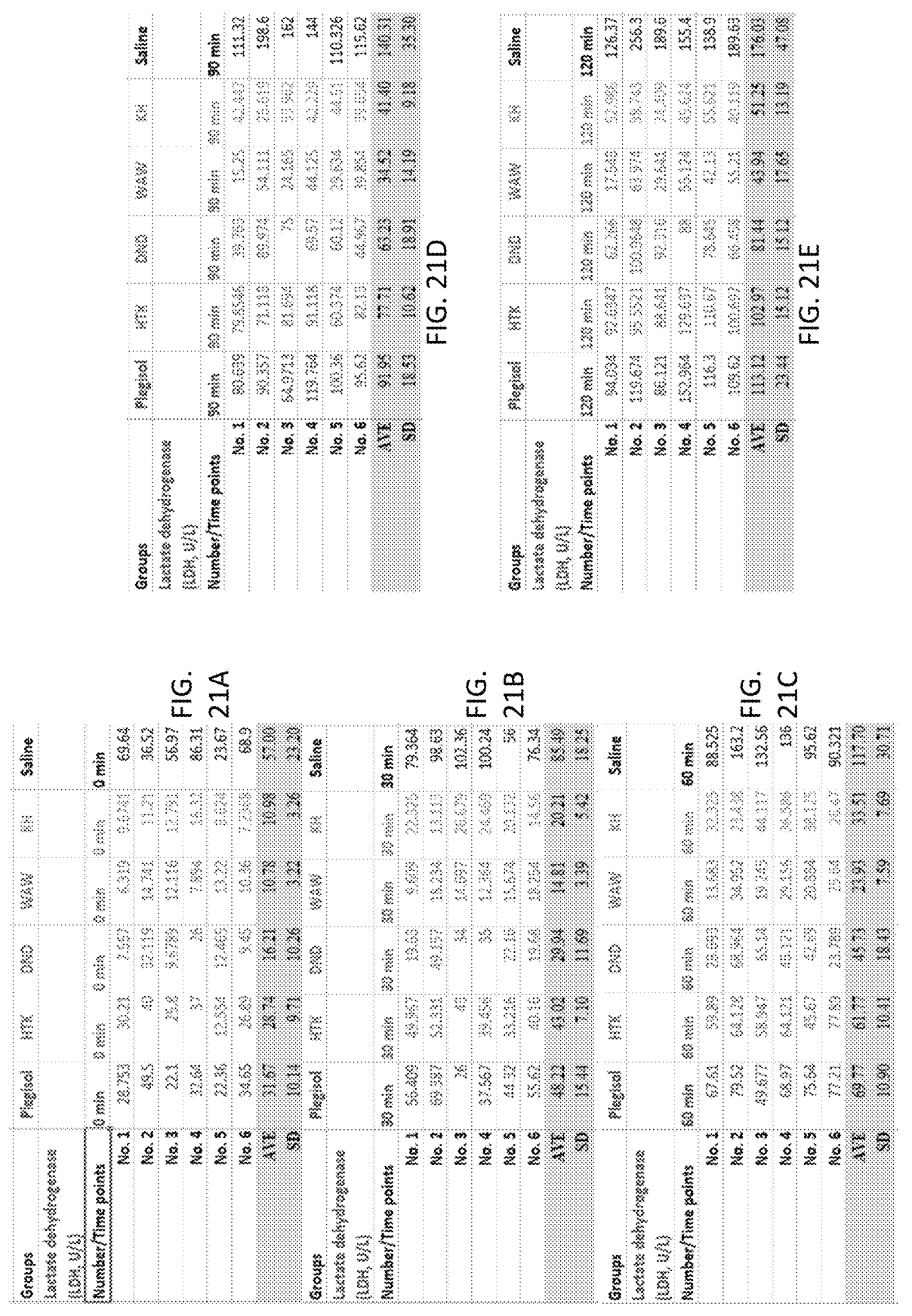

FIG. 21 shows data underlying FIG. 14 which is a comparison of lactate dehydrogenase (LDH) expression in U/L over time of rat hearts treated with each of the five solutions under study labelled including Plegisol cardioplegic solution labelled Plegisol, HTK cardioplegic solution labelled HTK, the del Nido cardioplegic solution labelled as DND, the cardioplegic solution WAW formulation of the present invention of FIG. 15 with 20 mmol/L THAM concentration labelled as WAW, the positive control KH buffer solution labelled KH and the negative control saline solution labelled Saline.

DETAILED DESCRIPTION OF THE INVENTION

As used in this specification and in claims which follow, the singular forms "a", "an" and "the" include plural referents unless the context clearly indicates otherwise. Thus, for example, reference to "an ingredient" includes mixtures of ingredients, reference to "an active pharmaceutical agent" includes more than one active pharmaceutical agent, and the like.

As used herein, the term "about" as a modifier to a quantity is intended to mean+ or −5% inclusive of the quantity being modified.

As used herein, the term "effective amount" or "a therapeutically effective amount" of a drug or pharmacologically active agent is intended to mean a nontoxic but sufficient amount of the drug or active agent for providing the desired therapeutic effect. The amount that is "effective" will vary from subject to subject, depending on the age and general condition of the individual, the particular active agent or agents, and the like. An appropriate "effective" amount in any individual case may be determined by one of ordinary skill in the art using routine experimentation.

Figure 1:
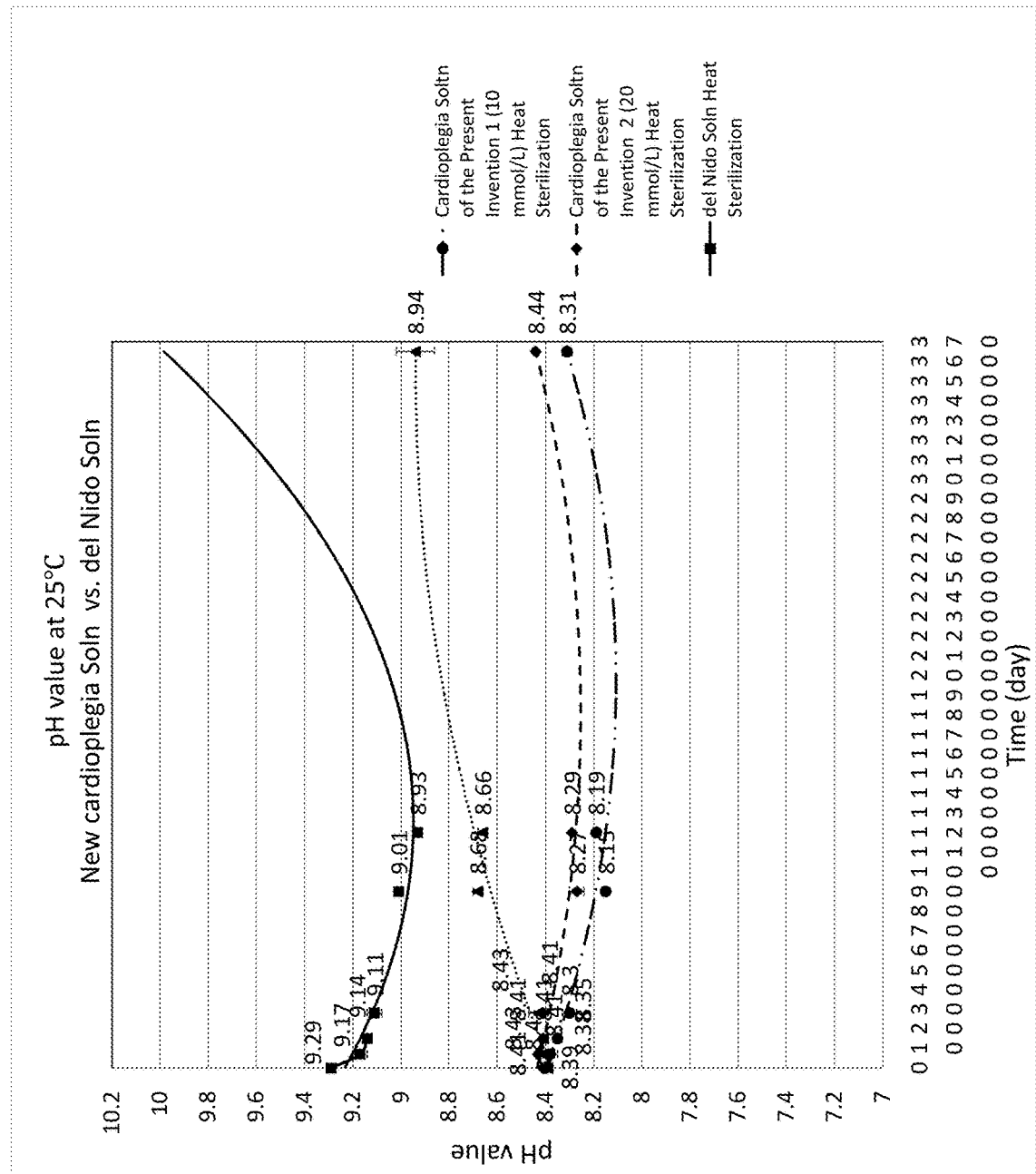
FIG. 1 is a graph with pH value on the Y axis and number of days indicated on the X axis comparing pH value of the cardioplegic solution of four cardioplegic solutions under study including the cardioplegic solution of the presentation invention WAW formulation of FIG. 15 with 10 mmol/L THAM, the cardioplegic solution of the presentation invention WAW formulation of FIG. 15 with 20 mmol/L THAM as well as the del Nido solution treated with heat sterilization process and the del Nido solution treated with filter sterilization process, respectively, stored at 25° C.
Figure 2:
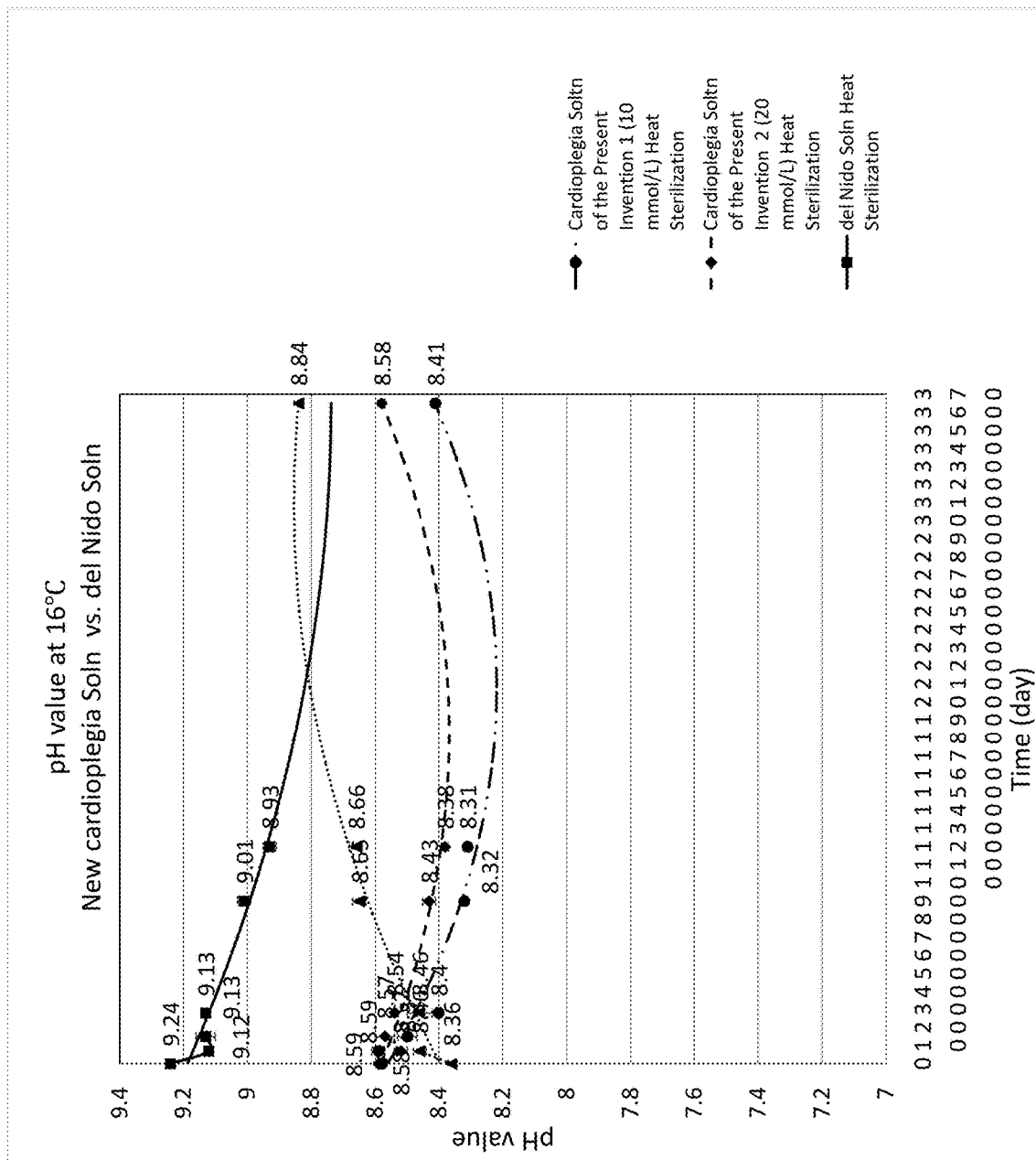
FIG. 2 is a graph with pH value on the Y axis and number of days indicated on the X axis comparing pH value of the cardioplegic solution under study including the cardioplegic solution of the present invention WAW formulation of FIG.

The cardioplegic solution of the present invention addresses drawbacks of the del Nido solution described in the background section while performing substantially better than the del Nido solution at preserving heart functions. Specifically, the Applicants have unexpectedly discovered that by replacing sodium bicarbonate of the del Nido solution with tris(hydroxymethyl)aminomethane (THAM), a.k.a. Tris or tromethamine at a proper concentration, the cardioplegic solution of the present invention does not form particulate matter as result of application of heat sterilization process as demonstrated by the Examples below in conjunction with FIGS. 4A and 4B. Furthermore, the cardioplegic solution of the present invention demonstrates pH and osmolality stability in storage for up to 365 days at a pH level that maintains critical levels of ions required for inducing cardioplegia as shown in FIGS. 1-3 as well as osmolality that does not exceed harmful levels for the human body as shown in FIG. 5. In addition, the only components that may be added prior to use are fully oxygenated patient blood and/or lidocaine, and these components are optional as per cardiac surgeon's requirement, substantially reducing the likelihood of human error in preparing the cardioplegic solution for use in comparison to the current practice for del Nido solution of manually mixing all the components. Importantly, studies presented in the Example section below in conjunction with FIGS. 6-14 demonstrate that the cardioplegic solution of present invention is surprisingly better at preserving heart functions than other cardioplegic solutions, including the del Nido cardioplegic solution. For example, the cardioplegic solution of the present invention is shown to reduce cell apoptosis based on BCL-2 and BAX/BCL-2 ratio as discussed in Examples below in connection with FIGS. 6 and 7. Furthermore, compared to the del Nido solution, the cardioplegic solution of the present invention is also shown to be substantially better at preserving heart function for rat hearts as indicated by experimental results for electrocardiography (ECG), left ventricle systolic pressure (LVSP), left ventricle diastolic pressure (LVDP), heart rate (HR), coronary flow (CF) and lactate dehydrogenase (LDH) experimental results discussed in the Examples below in connection with FIGS. 8-14.

Notably, Applicants are the first to discover that substituting sodium bicarbonate with THAM at proper concentration would not only eliminate cardioplegic solution instability such as formation of particulate matter as result of heat sterilization process but also substantially improve preservation of heart functions discussed above. Specifically, the Applicants are not aware of any prior art that suggest any of these properties by replacing sodium bicarbonate with THAM in the del Nido solution. For example, U.S. patent application Ser. No. 15/325,501 Volgushev teaches that THAM is not necessary and may be substituted with any pharmaceutically acceptable bases such as sodium bicarbonate. ('501 patent application, para. 0023). This contradicts findings in the Examples below in connection with FIGS. 1-3 which show that, unlike THAM, sodium bicarbonate causes stability issues that prevent commercialization of the del Nido solution. Additionally, the '501 patent application only addresses the issue of maintaining a certain range of pH, specifically maintaining lower limit of pH below 8 which is substantially lower than the cardioplegic solution of the present invention, rather than overall stability of the solution such as formation of precipitates during storage. ('501 patent application, para. 0022 and claims 1, 2, 3 and 4). Furthermore, the '501 patent application describes cardioplegic solutions that differs substantially from the present invention in composition and method of preparing the composition. For example, the cardioplegic solutions described in the '501 patent application does not contain sodium nor gluconate, each of which comprises the cardioplegic solution of the present invention and prepares its solution using different compounds. ('501 patent application, paras. 0047-0081 and claims 1-4). The osmolality of the cardioplegic solutions described in the '501 application is also substantially higher at above 400 mOsm/kg than the cardioplegic solution of the present invention and pH is also lower at below 8 as mentioned earlier in this paragraph. ('501 patent application, paras. 0022, 0025 and 0026).

Since the Applicant is the first to discover that modifying the del Nido solution by replacing sodium bicarbonate with THAM at proper concentrations eliminates the problem of particulate matter formation by heat sterilization and provides pH stability for at least 365 days thereby rendering the solution commercializable, the Phair doctrine should apply to the present invention to provide patentability to the present invention. Specifically, "the Phair doctrine," *Ex parte Phair*, 1 USPQ 133, 134 (Bd. App. 1929), held that "invention may exist in the discovery of the cause of a defect in an existing machine or process and applying a remedy therefor even though, after the cause is understood, the remedy would be obvious." The court espoused this doctrine in *In re Sponnoble*, 405 F.2d 578, 56 CCPA 823, 160 USPQ 237 (1969), which has been followed in later cases. In Sponnoble, on the basis of extensive evidence recited in the opinion, we found "a clear indication that he [Sponnoble] discovered the source of the problem." 405 F.2d at 585, 56 CCPA at 833, 100 USPQ at 243. Similarly, in the instant patent application, the Applicants have disclosed ample evidence in our Examples below and accompanying figures that replacement of sodium bicarbonate with THAM at proper concentration solves del Nido's particulate matter formation issues during heat sterilization rendering the cardioplegic solution of the present invention commercializable.

An embodiment of the cardioplegic solution of the present invention comprises potassium ($K^+$), magnesium ($Mg^{2+}$), sodium ($Na^+$), chloride ($Cl^-$), gluconate, acetate, sulfate ($SO_4^{2-}$), THAM and mannitol. In an embodiment, fully oxygenated patient blood and/or lidocaine may be optionally added prior to use. An embodiment of the present invention is a composition comprising about 27 to about 33 mEq/L potassium ($K^+$), about 16 to about 20 mEq/L of magnesium ($Mg^{2+}$), about 120 to about 146 sodium ($Na^+$), about 106 to about 130 mEq/L chloride ($Cl^-$), about 20 to about 24 mmol/L gluconate, about 22 to about 28 mmol/L acetate, about 6 to about 9 mmol/L sulfate ($SO_4^{2-}$), about 5 to about 30 mmol/L THAM and about 2 to about 5 g/L mannitol dissolved in water. Another embodiment of the present invention is a composition comprising about 29.63 mEq/L potassium ($K^+$), about 18.39 mEq/L of magnesium ($Mg^{2+}$), about 133.80 sodium ($Na^+$), about 118.51 mEq/L chloride ($Cl^-$), about 21.98 mmol/L gluconate, about 25.81 mmol/L acetate, about 7.76 mmol/L sulfate ($SO_4^{2-}$), about 10 mmol/L THAM or, alternatively, about 20 mmol/L THAM and about 3.116 g/L mannitol dissolved in water. In an embodiment, the water is distilled water and may be sterile. In another embodiment, the cardioplegic solution of the present invention is free of calcium ($Ca^{2+}$). In yet another embodiment of the present invention, the cardioplegic solution of the present invention is free of sodium bicarbonate. Any of the embodiments of the present invention may further comprise lidocaine at concentration of about 0.1 to about 0.14 mg/mL within the resulting solution. In addition, any of the embodiments of the present invention may further comprise fully oxygenated blood of the patient at a ratio of about 1:1 to about 1:8 ratio by volume of the fully oxygenated blood of the patient to solution of the present invention WAW formulation. In yet another embodiment, another polarizing agent such as procaine is used instead of lidocaine. In another embodiment, another pharmaceutically acceptable acids acid other than glacial acetic acid may be used such as hydrochloric acid, phosphoric acid and lactated acid.

The present invention also provides a method for preparing the cardioplegic solution of the present invention comprising a first step of mixing about 75 to about 95 mmol/L of sodium chloride (NaCl), about 20 to about 24 mmol/L of sodium gluconate ($C_6H_{11}NaO_7$), about 22 to about 28 mmol/L of sodium acetate trihydrate USP ($C_2H_3NaO_2 \cdot 3H_2O$), about 27 to about 33 mmol/L of potassium chloride USP (KCl), about 1.2 to about 1.6 mmol/L of magnesium chloride USP ($MgCl_2 \cdot 6H_2O$), about 6 to about 9 mmol/L of magnesium sulfate USP ($MgSO_4 \cdot 7H_2O$) and about 15 to about 20 mmol/L of mannitol USP ($C_6H_{14}O_6$). In another embodiment, the first step of the method for preparing the cardioplegic solution of the present invention comprises mixing about 86.02 mmol/L of sodium chloride (NaCl), about 21.99 mmol/L of sodium gluconate ($C_6H_{11}NaO_7$), about 25.85 mmol/L of sodium acetate trihydrate USP ($C_2H_3NaO_2 \cdot 3H_2O$), about 29.59 mmol/L of potassium chloride USP (KCl), about 1.41 mmol/L of magnesium chloride USP ($MgCl_2 \cdot 6H_2O$), about 7.76 mmol/L of magnesium sulfate USP ($MgSO_4 \cdot 7H_2O$) and about 17.1 mmol/L of mannitol USP ($C_6H_{14}O_6$). In an embodiment, the water is distilled water and may be sterile. The method for preparing the cardioplegic solution of the present invention further comprises a second step of mixing THAM and a pharmaceutically acceptable acid to the solution resulting from the first step of the method in order adjust the solution to desired pH range of about 8.2 to about 8.6 as well as to achieve between about 5 mmol/L to about 30 mmol/L of THAM concentration, about 10 mmol/L to 20 mmol/L of THAM concentration, about 10 mmol/L of THAM concentration or about 20 mmol/L of THAM concentration. In an embodiment, the pharmaceutically acceptable acid comprises glacial acetic acid. Such a composition may be mixed up to 365 days before use. In an embodiment, the method of the present invention may optionally further comprise the step of mixing lidocaine and/or fully oxygenated blood of the patient to the solution resulting from steps 1 and 2 of the method for preparing the cardioplegic solution of the present invention prior to use.

In an embodiment, the method for preparing the cardioplegic solution of the present invention comprises the step of mixing into per 1 liter of Plasma-Lyte A solution about 15 to about 19 mmol mannitol, about 5 to about 10 mmol magnesium sulfate, and about 22 to about 27 mmol potassium chloride. In another embodiment, the first step of method for preparing the cardioplegic solution of the present invention comprises mixing into per 1 liter of Plasma-Lyte A solution about 17.10 mmol mannitol, 7.76 mmol magnesium sulfate, and 24.85 mmol potassium chloride. The Plasma-Lyte A base solution, in turn, contains per liter about 140 mEq/L sodium $Na^+$, about 5 mEq/L potassium $K^+$, about 3 mEq/L magnesium $Mg^{2+}$, about 98 mEq/L chloride $Cl^-$, about 27 mEq/L acetate, and about 23 mEq/L gluconate. The method for preparing the cardioplegic solution of the present invention further comprises a second step of mixing THAM and a pharmaceutically acceptable acid to the solution resulting from the first step of the method in order adjust the solution to desired pH range of about 8.2 to about 8.6 as well as to achieve between about 5 mmol/L to about 30 mmol/L of THAM concentration, about 10 mmol/L to 20 mmol/L THAM concentration, about 10 mmol/L of THAM concentration or about 20 mmol/L of THAM concentration. In another embodiment, another polarizing agent such as procaine is used instead of lidocaine.

In an embodiment of the present invention, the cardioplegic solution prepared using any of the method of the present invention disclosed comprises about 29.63 mEq/L $K^+$, about 18.39 mEq/L of $Mg^{2+}$, about 133.80 $Na^+$, about 118.51 mEq/L $Cl^-$, about 21.98 mmol/L gluconate, about 25.81 mmol/L acetate, about 7.76 mmol/L sulfate, about 5 mmol/L to 30 mmol/L THAM and about 3.116 g/L mannitol dissolved in water. In an embodiment, the cardioplegic solution prepared using the method of the present invention is free of sodium bicarbonate. In an embodiment, the cardioplegic solution prepared using the method of the present invention is free of calcium.

The present invention also provides a method for administering any of the cardioplegic solution disclosed herein to a patient during cardiac surgery to induce cardioplegia comprising any administration methods that are currently used to induce cardioplegia using the del Nido solution. In an embodiment, method for administering any of the cardioplegic solution of the present invention disclosed herein to a patient during cardiac surgery to induce cardioplegia comprises the step of rapidly perfusing the patient's heart with a cardioplegic solution of the present invention. In one embodiment, 20-30 mL/kg of cardioplegic solution of the present invention is used for perfusion. The storage temperature of the cardioplegic solution may range from about 4° C. to about room temperature.

In one embodiment, cardioplegia is delivered into the root of a cross-clamped aorta and/or directly into the coronary sinus. In an embodiment, a cardioplegia catheter is a balloon-cuffed catheter that is placed through the right atrium into the coronary sinus and is used to perfuse the coronary circulation through the venous circulation. This has the advantage of more uniform distribution in patients with diffuse coronary artery disease and is not dependent on a competent aortic valve for delivery.

In an embodiment of the present invention, the process of the present invention for using a cardioplegic solution disclosed herein during cardiac surgery to induce temporary cardiac arrest includes perfusing the patient's heart with a cardioplegic solution of the present invention having a temperature of about 4 to about 35 degrees centigrade, preferably about 10 to about 21 degrees centigrade, and most preferably about 13 degrees centigrade. It will be generally understood by those skilled in the art that the process for preserving a patient's heart for cardioplegia of this invention includes perfusing the heart with the aqueous solution at moderate hypothermia. The process of this invention includes perfusing the heart with a volume of about 20-30 mL/kg of the solution. Another practice of this invention provides a process for preserving a patient's heart for cardioplegia which includes perfusing the heart with the aqueous solution of this invention about once each 20 to 40 minutes at moderate hypothermia. The process of this invention may include perfusing the heart with the aqueous solution of this invention on about 20 to 40 minute cycles for at least about 24 cycles at moderate hypothermia. In another practice of this invention includes continuous delivery of cardioplegic solution.

In any of the embodiments described, the cardioplegic solution of the present invention maintains a pH of about 8.2 to about 8.6, about 8.3 to about 8.5 or about 8.4. In any of the embodiments described, the cardioplegic solution of the present invention maintains a concentration of THAM between about 5 mM to about 30 mM, or between about 5 mM to about 20 mM, about 10 mM or about 20 mM. In one embodiment, the composition of the present invention comprises 20 mM THAM concentration of the present invention with storage at about 25° C.

In an embodiment, any cardioplegic solution of the present invention disclosed is stored at about 4° C. to about 25° C. degrees centigrade to ensure stability in pH, prevention of precipitate formation and osmolality. In an embodiment, any cardioplegic solution of the present invention disclosed is stored at about 4° C. to about 16° C. degrees centigrade to ensure stability of pH, precipitate formation and osmolality. In yet another embodiment, any cardioplegic solution of the present invention disclosed is stored at about 16° C. degrees centigrade to ensure stability of pH, precipitate formation and osmolality.

Examples

Stability Studies

Three stability studies were conducted on the cardioplegic solution of the invention to the del Nido solution to compare pH, particulate matter formation and osmolality stability in storage at 25° C., 16° C. and 4° C. up to 365 days. The four cardioplegic solutions studied were two embodiments of the present invention WAW formulations of FIG. 15 and two del Nido cardioplegic solutions. Specifically, the two embodiments of the present invention involved in the stability study were a first solution comprising about 29.63 mEq/L $K^+$, about 18.39 mEq/L of $Mg^{2+}$, about 133.80 mEq/L $Na^+$, about 118.51 mEq/L $Cl^-$, about 21.98 mmol/L gluconate, 25.81 mmol/L acetate, 7.76 mmol/L $SO_4^{2-}$, and about 3.116 g/L mannitol with THAM concentration of about 10 mM in water per total volume of 1000 mL whereas the second solution of the present invention differed from the first solution only in THAM concentration of about 20 mM rather than about 10 mM. Both solutions of the present invention were treated with heat sterilization process. The first del Nido cardioplegic solution involved in the stability studies was also treated with heat sterilization process while the second del Nido cardioplegic solution involved in the stability studies was treated with filter sterilization process rather than the heat sterilization process.

For each of the four cardioplegic solutions, data was taken on Day 1, Day 7, Day 14, Day 28, Day 90, Day 120 and Day 365 of storage stored at 4° C., 16° C. and 25° C. after sterilization. Sterilization by heat involved using autoclave heating the solution to 121° C. and maintaining the temperature for 15 minutes.

pH stability required that the pH of each cardioplegic solution stayed within the range of about 8.2 to about 8.6 which is the pH required to attenuate metabolic acidosis during cardio arrest. Particulate matter stability required that particle matter$>=10$ μm remained equal or below concentration of 25/mL and particle matter$>=25$ μm remained equal or below concentration of 3/mL, which are criteria set forth by United States Pharmacopeia (USP) for acceptable particulate presence in a pharmaceutical solution. Osmolality stability required that osmolality stayed below 388 mOsm/kg which is the limit safe in human bodies as observed by commercialized products containing THAM such as THAM Hospira which 0.3 M solution has an osmolarity of 389 mOsm/L.

pH Stability Study

FIGS. 1, 2 and 3 illustrate pH stability results for storage temperatures at 25° C., 16° C. and 4° C., respectively, over 365 days for the two embodiments of the cardioplegic solution of the present invention and the two the del Nido solution treated with heat sterilization and filter sterilization, respectively.

FIG. 1 shows pH stability results for storage at 25° C. As shown in FIG. 1, only the cardioplegic solution of the present invention WAW formulation with about 20 mM THAM concentration satisfied the pH stability of maintaining pH between 8.2-8.6 for all 365 days of storage. pH of the cardioplegic solution of the present invention WAW formulation with about 10 mM THAM concentration decreased below 8.2 between about $80^{th}$ and $310^{th}$ days. Nevertheless, both cardioplegic solutions of the present invention demonstrated substantially more pH stability over 365 days than both del Nido solutions. For example, the del Nido solution treated with heat sterilization process stayed outside of the acceptable range at above pH 8.6 for the entire duration of the testing period, and del Nido solution treated with filter sterilization process stayed within the pH 8.2 to 8.6 only for the first 90 days, after which the pH stayed above 8.6 for the remainder of the test.

FIG. 2 illustrates pH stability results for storage at 16° C. As shown in FIG. 2, pH of both cardioplegic solutions of the present invention WAW formulation maintained the required pH 8.2 and 8.6 range throughout the entire testing period of 365 days. In contrast, pH of both del Nido solutions did not maintain pH between 8.2 and 8.6. Specifically, the del Nido solution treated with heat sterilization process stayed above pH 8.6 for the entire duration of the testing period, and del Nido solution treated with filter sterilization process again stayed within the pH 8.2 to 8.6 only for the first 90 days, after which the pH stayed above 8.6 for the remainder of the test.

Finally, for storage at 4° C., as illustrated in FIG. 3, pH of the cardioplegic solution of the present invention WAW formulation with 10 mM THAM concentration decreased below 8.2 between about $150^{th}$ and $300^{th}$ days while pH of cardioplegic solution of the present invention WAW formulation with 20 mM THAM concentration rises above 8.6 from day zero to about day 30. As with storage at 16° C., pH of both del Nido solutions remained outside of the 8.2-8.6 criteria for most if not all the testing period. For example, the del Nido solution treated with heat sterilization process stayed above pH 8.6 for the entire duration of the testing period, and del Nido solution treated with filter sterilization process stayed within the pH 8.2 to 8.6 only for the first 90 days, after which the pH stayed above 8.6 for the remainder of the test.

Therefore, as seen in FIGS. 1, 2 and 3 both embodiments of the cardioplegic solutions of the present invention WAW formulation demonstrated substantially more pH stability than both del Nido solutions in all three storage temperatures 4° C., 16° C. and 25° C. FIG. 3 illustrates that the 20 mM THAM concentration solution of the present invention WAW formulation resulted in the most stable pH over the 365 days of testing. Therefore, in one embodiment, the composition of the present invention is that of the WAW formulation of FIG. 15 with about 20 mM THAM concentration of the present invention with storage at 25° C. In addition, FIG. 2 illustrates that an embodiment of the present invention WAW formulation with 10 mM as well as an embodiment of the present invention WAW formulation with 20 mM THAM concentration maintained pH within the 8.2 to 8.6 range throughout the testing period. Therefore, another embodiment of the present invention comprises the composition WAW formulation of FIG. 15 with 10 mM THAM concentration stored at 16° C. In yet another embodiment of the present invention comprises the composition WAW formulation of FIG. 15 with 20 mM THAM concentration stored at 16° C.

Particulate Matter Stability Study

FIGS. 4A and 4B illustrate results of the particulate matter stability results. As illustrated in FIGS. 4A and 4B, the del Nido solution sterilized using heat process completely failed the particulate matter test whereas all three other solutions satisfied particle matter test for the entirety of the test period of 365 days. Specifically, the del Nido solution sterilized using heat process exceeded acceptable range immediately at day zero for both particle matter of size$>=10$ μm as well as particle matter of size$>=25$ μm. Although for particle size$>=10$ μm, the number of particles decreased to within acceptable range during part of the observation period as evidenced by data taken at day 7, day 15 and day 28 illustrated in FIG. 4A, the number of particles again exceeded acceptable range at and after day 90. Similarly, for particle size$>=25$ μm illustrated in FIG. 4B, although the number of particles decreased to within acceptable range only during part of the observation period as evidenced by data taken at day 15 and day 28, the number of particles again exceeded acceptable range at and after day 90. As discussed above, this result is significant as heat sterilization is a preferred common procedure for commercialization, rendering the del Nido solution difficult to commercialize whereas the cardioplegic solution of the present invention has solved this problem and making it commercializable. Therefore, one embodiment of the present invention provides a cardioplegic solution with 29.63 mEq/L K$^+$, about 18.39 mEq/L of Mg$^{2+}$, about 133.80 Na$^+$, about 118.51 mEq/L Cl$^-$, about 21.98 mmol/L gluconate, 25.81 mmol/L acetate, 7.76 mmol/L SO$_4^{2-}$, about 3.116 g/L mannitol with THAM concentration of between about 10 mM and about 20 mM in water each sterilized using heat sterilization process.

Osmolality Stability Study

FIG. 5 illustrates results of the osmolality stability study. As shown in FIG. 5, all four cardioplegic solutions fall within the acceptable 388 mOsm/kg criteria. Notably, the cardioplegic solution of the present invention WAW formulation with THAM concentration of 20 mM demonstrated the highest osmolality of the four cardioplegic solutions whereas the cardioplegic solution of the present invention WAW formulation with THAM concentration of 10 mM demonstrated similar osmolality as the del Nido solution sterilized with filtering process.

Cardioplegic Arrest Study

Male Sprague-Dawley rats of about 350 to about 450 grams were used as study subjects and divided into three groups according to the three cardioplegic solutions studied: del Nido solution group (D), the cardioplegic solution of the present invention WAW solution group (W) and HTK solution group (H). Each group involved n=5+1 rats as study subjects. The cardioplegic solution of the present invention used in the cardioplegic arrest study comprises about 29.63 mEq/L $K^+$, about 18.39 mEq/L of $Mg^{2+}$, about 133.80 $Na^+$, about 118.51 mEq/L $Cl^-$, about 21.98 mmol/L gluconate, 25.81 mmol/L acetate, 7.76 mmol/L $SO_4^{2-}$ and about 20 mmol/L THAM and about 3.116 g/L mannitol.

Each rat was anesthetized with Isoflurane by anesthesia vaporizer machine and then heparinized intraperitoneally at 3000 U/kg following proper anesthesia. Each rat heart is then isolated and placed in a container with a small amount of ice cold Kerbs-Henseleit buffer (KHB). Each heart's aorta and left atrium were then cannulated followed by perfusion using the cardioplegic solution corresponding to each solution group by hand injection at 20 mL/kg for W and D solutions and 30 mL/kg for H solution, with the perfusion time being 10 minutes and the temperature of the cardioplegic solution being about 8° C. After perfusion, each heart was placed in a container with small amount of KHB on ice. Samples are then collected from each heart at specific points in time, specifically 0, 2, 4, 6 and 12 hours after perfusion with each solution. For Histopathological sections, samples are collected at 0, 4 and 12 hours after perfusion with each solution. The collected samples were stored at −80° C. immediately. Bcl-2 and Bax/Bcl-2 ratio parameters were examined using the samples collected.

Bcl-2

Apoptosis-promoting effects from both effectors and activators are inhibited by direct interaction with anti-apoptotic Bcl-2 family members[3,4,5]. In preclinical models, Bcl-2 binds and sequesters BH3-only activators and prevents them from interacting with pore-forming effectors[6,7,8]. Likewise, Bcl-2 can directly influence effectors to prevent mitochondrial pore-formation. The dynamic balance that occurs between anti-apoptotic members, such as Bcl-2, and pro-apoptotic members helps determine whether the cell initiates apoptosis.

[3]Shamas-Din A, Kale J, Leber B, Andrews D W. Mechanisms of action of Bcl-2 family proteins. Cold Spring Harb Perspect Biol. 2013:5(4)
[4]Portt, L.; Norman, G.; Clapp, C.; Greenwood, M.; Greenwood, T. M. Anti-apoptosis and cell survival: A review. Biochim. Biophys. Acta 2011, 1813, 238-259.
[5]Hata A N, Engelman J A, Faber A C. The BCL2 Family: Key Mediators of the Apoptotic Response to Targeted Anticancer Therapeutics. Cancer Discov. 2015; 5(5):475-87.
[6]Shamas-Din A, Kale J, Leber B, Andrews D W. Mechanisms of action of Bcl-2 family proteins. Cold Spring Harb Perspect Biol. 2013; 5(4)
[7]Portt, L.; Norman, G.; Clapp, C.; Greenwood, M.; Greenwood, T. M. Anti-apoptosis and cell survival: A review. Biochim. Biophys. Acta 2011, 1813, 238-259.
[8]Hata A N, Engelman J A, Faber A C. The BCL2 Family: Key Mediators of the Apoptotic Response to Targeted Anticancer Therapeutics. Cancer Discov. 2015; 5(5):475-87.

Results of the Bcl-2 Western blot illustrated by FIGS. 6A and 6B demonstrate that following application of the glycolysis enzyme and apoptosis initiator GAPDH, the cardioplegic solution of present invention W is associated with higher level of Bcl-2 expression than the del Nido cardioplegic solution D, and, therefore, the cardioplegic solution WAW formulation W of the present invention inhibits apoptosis more so than the del Nido cardioplegic solution. Therefore, a method of the present invention provides a method for cardioplegia that inhibits apoptosis.

Bax

Bax is reported to interact with, and increase the opening of, the mitochondrial voltage-dependent anion channel (VDAC), which leads to loss in membrane potential and the release of cytochrome $c^9$. The expression of this gene is regulated by the tumor suppressor P53 and has been shown to be involved in P53-mediated apoptosis.

[9]V. Shoshan-Barmatz, D. Ben-Hail, L. Admoni, Y. Krelin, S. S. Tripathi. The mitochondrial voltage-dependent anion channel 1 in tumor cells. Biochim. Biophys. Acta, 1848 (10) (2015), pp. 2547-2575.

Bax/Bcl-2 Ratio

The mitochondrial-mediated pathway of apoptosis is regulated by the Bcl-2 family of antiapoptotic (Bcl-2, Bcl-XL, Mcl-1) and proapoptotic proteins (Bax, Bad and Bak), and Bcl-2 inhibits apoptosis by interacting and forming inactivating heterodimers with Bax-Bak. It has been suggested that the Bax/Bcl-2 ratio may be more important than either promoter alone in determining apoptosis.[10,11] The Bax/Bcl-2 ratio is a measure of a cell's vulnerability to apoptosis. A high Bax/Bcl-2 ratio is associated with greater vulnerability to apoptotic activation, while a high caspase-3 level is often associated with apoptotic activity.[12]

[10]Raisova M, Hossini A M, Eberle J, Riebeling C, Weider T, Sturm I, et al. The bax/bcl-2 ratio determines the susceptibility of human melanoma cells to CD95/Fas-mediated apoptosis. J Invest Dermatol 2001; 117 (2): 333-340
[11]Del P. G., Venditti A., del P. M., Maurillo L., Buccisano F., Tamburini A., Cox M. C., Franchi A., Bruno A., Mazzone C. Amount of spontaneous apoptosis detected by Bax/Bcl-2 ratio predicts outcome in acute myeloid leukemia (AML). Blood. 2003; 101: 2125-2131. 10.1182/blood-2002-06-1714
[12]Jarskog L F, Selinger E S, Lieberman J A, Gilmore J H. Apoptotic proteins in the temporal cortex in schizophrenia: high Bax/Bcl-2 ratio without caspase-3 activation. Am J Psychiatry 2004; 161: 109-115.

As shown in FIG. 7, the Bax/Bcl-2 ratio for the cardioplegic solution of the present invention WAW formulation is substantially lower than that of the del Nido solution N at each datapoint. Therefore, a method of the present invention provides a method for cardioplegia that inhibits apoptosis using the cardioplegic solution of the present invention.

Comparison of the Effect of Cardioplegic Solution-Mediated Cardioprotection in Rat Isolated Hearts Experimental Animals—Male Sprague-Dawley rats weighing between 300 and 400 g, 6 in each group, were the subjects of this study. The experimental protocols of heart isolation and ex vivo incubation were approved by the Institutional Animal Care and Use Committee.

Cardioplegic solutions—the cardioplegic solution of the present invention (WAW), del Nido, Plegisol, HTK, KH buffer, and saline solutions were prepared. The cardioplegic solution of the present invention WAW used in this study comprises about 29.63 mEq/L $K^+$, about 18.39 mEq/L of $Mg^{2+}$, about 133.80 $Na^+$, about 118.51 mEq/L $Cl^-$, about 21.98 mmol/L gluconate, 25.81 mmol/L acetate, 7.76 mmol/L $SO_4^{2-}$ and about 20 mmol/L THAM and about 3.116 g/L mannitol.

Preparation of Isolated Perfused Hearts. The rats are anesthetized by intraperitoneal injection of sodium pentobarbital (60 mg/kg) for heart isolation described above. Each animal then received an intravascular injection of heparin (500 U/mL) after abdominal incision via the vena cava 3 min before removal of the heart. After thoracotomy, each heart was quickly excised and submerged in KH buffer or cardioplegic solution corresponding to its experimental group at 10-15° C. and flushed with the same solution 5 times via aorta to remove blood residues. Each heart was then weighted and cannulated via the aorta and perfused with Kerbs-Henseleit (KH) buffer solution or cardioplegic solution at a rate of 20 mL/kg for cardioplegic solution of the present invention WAW formulation and del Nido, 30 mL/kg of HTK, 20 mL/kg of Plegisol and 10-20 mL/min (continuous infusion) of KH buffer respectively according to each cardioplegic solution experimental group, at 10-15° C. using a roller pump. After 2 hours of perfusion, each heart was mounted based on the Langendorff model[13], which involved retrograde perfusing the hearts with KH buffers solution (Sigma, St. Louis, MO) maintained at 37° C. under constant pressure (~95 mmHg). Each heart was then perfused without recirculation for the first 30 min for removal of cardioplegic solution and was then each perfused by recirculation with a fixed volume of 100 mL perfusate for the actual experiment for 20 minutes of basal recording as previously described. The reservoir of KH solution was continuously bubbled with 95% $O_2$/5% $CO_2$ and maintained at 37° C. by a heated water jacket. The following diagram shows the study protocol to evaluate cardiac function after treatment of various cardioplegic solutions.

[13]Bøtker, H. E., Hausenloy, D., Andreadou, I. et al. Practical guidelines for rigor and reproducibility in preclinical and clinical studies on cardioprotection. Basic Res Cardiol (2018) 113: 39

A separate study was done to induce acute myocardial IR injury in order to determine survival of heart cells after ischemia as well as myocardial infarct size and the results are illustrated in FIG. 8B. After a basal period of 30 min, each heart was subjected to 30 min of global, no-flow ischemia at 37° C., followed by 4 h of reperfusion as IR insult using cardioplegic solution corresponding to the cardioplegic study group. Control hearts are perfused for 290 min with KH solution.

Evaluation of cardiac mechanics. The coronary perfusion pressure (CPP) was monitored by pressure transducer connected to the side arm of the aortic cannula. The real-time left ventricular pressure-volume loops was measured by a PV catheter (ADVantage Pressure-Volume System, Transonic, Netherlands) inserted into the left ventricle via the same side arm of the aortic cannula. Coronary flow (CF) was determined by collection of perfusate for 30 seconds and calculated as mL/min/g after normalization of the wet weight of the heart. Then, 0.1 mL of perfusate was collected for the cardiac enzyme assay as described below. Pressure signals were recorded on a four-channel MP36 data acquisition system (Biopac Systems, Inc., CA) as previously described.

Cardiac enzyme assay. Perfusate or tissue homogenate of left ventricle as described below was centrifuged at 620 g, and the supernatant was collected and stored at -70° C. for further analysis of B-type natriuretic peptide, troponin I, creatine kinase MB, and lactate dehydrogenase (LDH) activity using commercial kits (Roche, Tokyo, Japan) to evaluate degree of myocardial injury as described previously.

Determination of myocardial infarct size using Triphenyltetrazolium chloride (TTC) staining. After perfusion, each heart was weighed and sliced into 2-mm sections from base to apex. There is a homogenous response to global ischemia in the isolated perfused heart model; therefore, only the middle slice with the maximum heart tissue was used to evaluate infarction. The evaluation was performed by staining with 1% 2,3,5-triphenyltetrazolium (Sigma) at 37° C. for 20 min to distinguish the infarct from the viable myocardial area as previously described by identifying the pale area which indicated infarct tissue and the red area which indicates the viable myocardial area. The remaining tissue slices were stored at -80° C. for further biochemical analysis or post-fixed with 4% paraformaldehyde for indirect immunofluorescence staining.

Western blot analysis. Cardiac tissues from the left ventricle were sampled and prepared as total protein, cytosolic, and mitochondrial fractions using a commercial kit (BioVision, Milpitas, CA). Protein samples were quantitated using a commercial assay kit (Bio-Rad, Hercules, CA) and then separated and electrophoretically transferred to polyvinylidene difluoride membranes as previous described. After blocking in 5% skimmed milk, the membranes were incubated overnight at 4° C. with antibodies against cytochrome c, BCL02, Bax, Bcl-$X_L$, caspase-9, Apaf-1, caspase-3 or inflammasome NLRP-3 (Santa Cruz Biotechnology Santa Cruz, CA). After washing, the membranes were incubated for 1 hour at room temperature with a corresponding horseradish peroxidase-conjugated IgG (Jackson ImmunoResearch, West Grove, PA). After washing the membranes, the bound antibody complex was detected using a commercial enhanced chemiluminescence kit (Thermo Scientific, Rockford, IL). The densities of the bands of appropriate molecular masses were determined semi-quantitatively by densitometry using an image analytic system (Diagnostic Instruments, Sterling Heights, MI).

Indirect immunofluorescence staining was performed to examine geometrical localization of protein expression in hearts as previous described. Specifically, 5-µm sections were fixed in 4% formaldehyde. After blocking for endogenous peroxidase, specific antibody was added, and the samples were incubated at 4° C. overnight. Anti-rabbit or anti-goat IgG was used as negative controls (Jackson ImmunoResearch). The next day, the slides were incubated with HRP-conjugated IgG for 1 hour at room temperature and developed using a tyramide signal amplification kit (PerkinElmer, MA). Nuclei were counterstained with 4',6-diamidino-2-phenylindole (DAPI).

Results for Cardioplegia Solutions in Isolated Rat Heart

FIGS. 8A and 8B illustrate survival rate of rat hearts during experimentation and myocardial infarct size respectively. As illustrated in FIG. 8A, rat heart survival rate during the experiment is highest for the positive control KH buffer followed by the cardioplegic solution of the present invention W. As seen in FIG. 8B, the cardioplegic solution of the present invention resulted in the smallest myocardial infract size by a substantial margin as compared to Plegisol, HTK and del Nido cardioplegic solution. Both results indicates that the cardioplegic solution of the present invention protects the hearts more so than all three other cardioplegic solutions Electrocardiography (ECG)—As illustrated in FIG. 9, ECG of the group treated with the cardioplegic solution of the present invention exhibits voltages higher than all other three cardioplegic solutions and are closest to the group treated with positive control KH buffer solution, indicating a healthier and better functioning heart. At 0, 30, 60, 90, and 120 min, the ECG of the rats treated with the cardioplegic solution of the present invention presented a higher and significantly different voltage compared with the rats treated with Plegisol, at $P<0.05$. At 0, 30, and 60 min, the ECG of the rats treated with the cardioplegic solution of the present invention presented a higher and significantly different voltage compared with the rats treated with HTK, at $P<0.05$. More importantly, at 0, 30, 60, 90, and 120 min, the ECG of the rats treated with the cardioplegic solution of the present invention presented a higher and significantly different voltage compared with the rats treated with del Nido solution, at P<0.05. In addition, at 0, 30, 60, 90, and 120 min, the ECG of the rats treated with the cardioplegic solution of the present invention is not significant different compared with the rats treated with KH buffer, at P<0.05. Therefore, these results demonstrate that the cardioplegic solution of the present invention produces superior results in maintaining higher electric potentials in treated hearts.

Left Ventricle Systolic Pressure (LVSP)—Similarly, as shown in FIG. 10, LVSP of the group treated with the cardioplegic solution of the present invention is substantially higher than that of all three other cardioplegic solutions and with results closest to the group treated with positive control KH buffer solution than any other cardioplegic solution. Statistical tests performed at P<0.05 indicate that LVSP of the rat hearts treated with Plegisol, HTK, and more importantly the del Nido solution were significantly different from that of rat hearts treated with the cardioplegic solution of the present invention at 0, 30, 60, 90, and 120 min. LVSP of the rat hearts treated with the cardioplegic solution of the present invention are more similar to that of rat hearts treated with KH buffer, the positive control, suggesting a superior ability of maintaining heart pressure as compared to Plegisol, HTK, and the del Nido solution.

Left Ventricle Diastolic Pressure (LVDP)—The real-time left ventricular pressure-volume loop was measured by a PV catheter (ADVantage Pressure-Volume System, Transonic, Netherlands) inserted into the left ventricle via the same side arm of the aortic cannula of the group treated with the cardioplegic solution of the present invention is higher than all three other cardioplegic solutions. As illustrated in FIG. 11, LVDP of the group treated with the cardioplegic solution of the present invention is substantially higher than all three other cardioplegic solutions and is closest to the group treated with the positive control KH buffer than any other cardioplegic solutions tested. The rat hearts treated with the cardioplegic solution of the present invention exhibited significantly different LVDP at 0, 30, 60, 90, and 120 min compared to Plegisol, HTK, and more importantly, the del Nido solution, at P<0.05. LVDP of the group treated with the cardioplegic solution of the present invention was more similar to that of KH buffer, the positive control, indicating the superiority of the cardioplegic solution of the present invention in maintaining healthy LVDP as compared to the other three cardioplegic solutions.

Heart Rate (HR)—As illustrated in FIG. 12, heart rate of the group treated with the cardioplegic solution of the present invention is substantially higher than all three other cardioplegic solutions and is closest to the group treated with the positive control KH buffer group. Heart rate of the rat hearts treated with the cardioplegic solution of the present invention was higher and significantly different at 0, 30, 60, and 90 min compared to that of rat hearts treated with Plegisol, HTK, and more importantly, the del Nido solution, at P<0.05. The similarity of heart rate of hearts treated with the cardioplegic solution of the present invention to that of hearts treated with KH buffer, as compared to those treated with Plegisol, HTK, and the del Nido solution, indicates a superior ability of the cardioplegic solution of the present invention in maintaining a healthy heart rate.

Coronary Flow (CF)—CF is the circulation of blood in the blood vessels that supply the heart muscle (myocardium). Coronary arteries supply oxygenated blood to the heart muscle, and cardiac veins drain away the blood once it has been deoxygenated. Because the rest of the body, and most especially the brain, needs a steady supply of oxygenated blood that is free of all but the slightest interruptions, the heart works constantly and sometimes works quite hard. Therefore its circulation is of major importance not only to its own tissues but to the entire body and even the level of consciousness of the brain from moment to moment. As illustrated in FIG. 13, coronary flow of the group treated with the cardioplegic solution of the present invention is substantially higher than all three other cardioplegic solutions. Coronary flow of rat hearts treated with the cardioplegic solution of the present invention was higher and significantly different at 0 and 30 min from that of rat hearts treated with Plegisol and HTK, at P<0.05. More importantly, coronary flow of rat hearts treated with the cardioplegic solution of the present invention was higher and significantly different at 0, 30, 60, 90, and 120 min from that of rat hearts treated with the del Nido solution, at P<0.05. As hearts treated with the solution of the present invention display coronary flow more similar to that of hearts treated with KH buffer, the positive control, as compared to hearts treated with the other three cardioplegic solutions, superiority of the cardioplegic solution of the present invention in its ability to maintain healthy coronary flow is suggested.

Lactate Dehydrogenase (LDH)—LDH is expressed extensively in body tissues and is a non-specific biomarker of organ damage. Since our study only involved one organ (isolated heart model), the elevated LDH indicated the extent of damage to the heart. As FIG. 14 illustrates, the cardioplegic solution of the present invention is associated with the least amount of LDH of the four cardioplegic solutions examined. LDH levels in rat hearts treated with the cardioplegic solution of the present invention were lower and significantly different than that of rat hearts treated with Plegisol and HTK at 0, 30, 60, 90, and 120 min, at P<0.05. More importantly, LDH levels in rat hearts treated with the cardioplegic solution of the present invention were lower and significantly different than that of rat hearts treated with the del Nido solution at 30, 60, 90, and 120 min, at P<0.05. The hearts treated with the cardioplegic solution of the present invention released less LDH than hearts treated with the other three cardioplegic solutions, suggesting superiority of the cardioplegic solution of the present invention in its ability to prevent tissue damage.

It can be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims.

It is to be understood that both the foregoing general description and the following detailed description are exemplary and explanatory only and are not restrictive of the invention, as claimed.

These and other changes can be made to the technology in light of the detailed description. In general, the terms used in the following disclosure should not be construed to limit the technology to the specific embodiments disclosed in the specification, unless the above detailed description explicitly defines such terms. Accordingly, the actual scope of the technology encompasses the disclosed embodiments and all equivalent ways of practicing or implementing the technology.

The invention claimed is:

1. A cardioplegic solution comprising potassium ($K^+$), magnesium ($Mg^{2+}$), sodium ($Na^+$), chloride ($Cl^-$), gluconate, acetate, sulfate ($SO_4^{2-}$), tris(hydroxymethyl)aminomethane (THAM) and mannitol dissolved in water, wherein the potassium ($K^+$) concentration is about 27 to about 33 mEq/L, the magnesium ($Mg^{2+}$) concentration is about 16 to about 20 mEq/L, the sodium ($Na^+$) concentration is about 120 to about 146 mEq/L, the chloride ($Cl^-$) concentration is about 106 to about 130 mEq/L, the gluconate concentration is about 20 to about 24 mmol/L, the acetate concentration is about 22 to about 28 mmol/L, the sulfate ($SO_4^{2-}$) concentration is about 6 to about 9 mmol/L, the THAM concentration is between about 5 to about 30 mmol/L, mannitol concentration is about 2 to about 5 g/L and the cardioplegic solution is capable of maintaining a pH of about 8.2 to about 8.6 for 365 days wherein the term "about" as a modifier to a quantity is intended to mean+ or −5% inclusive of the quantity being modified.

2. The cardioplegic solution of claim 1 wherein the potassium ($K^+$) concentration is about 29.63 mEq/L, the magnesium ($Mg^{2+}$) concentration is about 18.39 mEq/L, the sodium ($Na^+$) concentration is about 133.80 mEq/L, the chloride ($Cl^-$) concentration is about 118.51 mEq/L, the gluconate concentration is about 21.98 mmol/L, the acetate concentration is about 25.81 mmol/L, the sulfate ($SO_4^{2-}$) concentration is about 7.76 mmol/L, the THAM concentration is 20 mmol/L and mannitol concentration is about 3.116 g/L.

3. The cardioplegic solution of claim 1 further comprising lidocaine wherein the lidocaine concentration is about 0.1 mg/mL to about 0.14 mg/mL within the cardioplegic solution.

4. A cardioplegic solution and patient blood composition comprising fully oxygenated patient blood at a ratio of about 1:1 to about 1:8 ratio by volume of the fully oxygenated blood of the patient to the cardioplegic solution of claim 1.

5. The cardioplegic solution of claim 1, wherein the cardioplegic solution is calcium free.

6. The cardioplegic solution of claim 1, wherein the cardioplegic solution is free of sodium bicarbonate.

7. A method for preparing the cardioplegic solution of claim 1, comprising the first step of addition of sodium chloride, sodium gluconate, sodium acetate trihydrate, potassium chloride, magnesium chloride, magnesium sulfate and mannitol in water to form a solution; the second step of mixing THAM and glacial acetic acid to the solution resulting from the first step,
wherein the concentration of sodium chloride is about 75 to about 95 mmol/L, the concentration of sodium gluconate is about 20 to about 24 mmol/L, the concentration of sodium acetate trihydrate is about 22 to about 28 mmol/L, the concentration of potassium chloride is about 27 to about 33 mmol/L, the concentration of magnesium chloride is about 1.2 to about 1.6 mmol/L, the concentration of magnesium sulfate is about 6 to about 9 mmol/L and the concentration of mannitol is about 15 to about 20 mmol/L in water and wherein the step of mixing THAM and glacial acetic acid to the solution resulting from the first step of the method adjusts the solution to pH range of about 8.2 to about 8.6 as well as to achieve about 5 to about 30 mmol/L of THAM concentration.

8. The method of claim 7, wherein the concentration of sodium chloride is about 86.02 mmol/L, the concentration of sodium gluconate is about 21.99 mmol/L, the concentration of sodium acetate trihydrate is about 25.85 mmol/L, the concentration of potassium chloride is about 29.59 mmol/L, the concentration of magnesium chloride is about 1.41 mmol/L, the concentration of magnesium sulfate is about 7.76 mmol/L and the concentration of mannitol is about 17.1 mmol/L in water and wherein the step of mixing THAM and glacial acetic acid to the solution resulting from the first step of the method adjusts the solution to desired pH range of about 8.2 to about 8.6 as well as to achieve about 20 mmol/L or 10 mmol/L of THAM concentration.

9. The method of claim 7, further comprising the step of addition of lidocaine to a concentration of about 0.1 mg/mL to about 0.14 mg/mL within the cardioplegic solution.

10. A method of making a cardioplegic solution and patient blood composition comprising the step of addition of fully oxygenated blood of a patient at a ratio of about 1:1 to about 1:8 ratio by volume of the fully oxygenated blood of the patient to the cardioplegic solution of claim 1.

11. The method of claim 7, wherein the cardioplegic solution is free of calcium.

12. The method of claim 7, wherein the cardioplegic solution is free of sodium bicarbonate.

13. The method of claim 7, wherein the steps are performed up to 365 days prior to use.

14. A method for preparing the cardioplegic solution of claim 1 comprising the first step of mixing mannitol, magnesium sulfate, THAM, and potassium chloride to a base solution to form a solution, and
the second step of combining THAM and glacial acetic acid to the solution of the first step to adjust the solution to a pH of about 8.2 to about 8.6, wherein the base solution per liter consists of Na+, K+, Mg2+, Cl−, acetate and gluconate.

15. The method of claim 14, wherein mannitol, magnesium sulfate, THAM, and potassium chloride are added to the base solution up to 365 days prior to use.

16. The method of claim 14, further comprising the step of addition of lidocaine to a concentration of about 0.1 mg/mL to about 0.14 mg/mL within the cardioplegic solution.

17. The method of claim 14, wherein the cardioplegic solution is stored at room temperature.

18. A method for inducing temporary cardiac arrest comprising the step of administering the cardioplegic solution of claim 1 to a patient in need thereof during cardiac surgery.

19. The method of claim 18, wherein the cardioplegic solution is administered at hypothermia.

20. The method of claim 18, wherein the cardioplegic solution is administered at normothermia.

21. The method of claim 18, wherein the cardioplegic solution is administered once during surgery.

22. The method of claim 18, wherein the cardioplegic solution is administered more than once during surgery.

* * * * *